US007570979B2

(12) United States Patent
Cooper

(10) Patent No.: US 7,570,979 B2
(45) Date of Patent: Aug. 4, 2009

(54) METHODS AND APPARATUS FOR PATIENT MONITORING

(76) Inventor: Philip George Cooper, 8 Stevens Street, Pennant Hills, New South Wales 2121 (AU)

(*) Notice: Subject to any disclaimer, the term of this patent is extended or adjusted under 35 U.S.C. 154(b) by 1039 days.

(21) Appl. No.: 11/091,396

(22) Filed: Mar. 29, 2005

(65) Prior Publication Data

US 2005/0222502 A1   Oct. 6, 2005

Related U.S. Application Data

(60) Provisional application No. 60/558,364, filed on Mar. 30, 2004.

(51) Int. Cl.
*A61B 5/00* (2006.01)
(52) U.S. Cl. .................. 600/323; 600/331; 600/529
(58) Field of Classification Search ................. 600/323, 600/331, 529
See application file for complete search history.

(56) References Cited

U.S. PATENT DOCUMENTS

| | | | | |
|---|---|---|---|---|
| 4,086,915 A * | 5/1978 | Kofsky et al. | ................ | 600/330 |
| 4,796,636 A * | 1/1989 | Branstetter et al. | .......... | 600/330 |
| 5,482,034 A * | 1/1996 | Lewis et al. | ................. | 600/323 |
| 5,542,421 A * | 8/1996 | Erdman | ....................... | 600/477 |
| 5,795,292 A * | 8/1998 | Lewis et al. | ................. | 600/323 |
| 5,902,235 A * | 5/1999 | Lewis et al. | ................. | 600/323 |
| 6,171,258 B1 * | 1/2001 | Karakasoglu et al. | ....... | 600/529 |
| 6,421,549 B1 * | 7/2002 | Jacques | ....................... | 600/331 |
| 6,438,399 B1 * | 8/2002 | Kurth | .......................... | 600/323 |
| 6,498,942 B1 * | 12/2002 | Esenaliev et al. | ........... | 600/310 |
| 6,615,065 B1 * | 9/2003 | Barrett et al. | ............... | 600/340 |
| 6,711,425 B1 * | 3/2004 | Reuss | .......................... | 600/331 |
| 6,811,538 B2 * | 11/2004 | Westbrook et al. | .......... | 600/529 |
| 6,839,580 B2 * | 1/2005 | Zonios et al. | ............... | 600/323 |
| 7,297,119 B2 * | 11/2007 | Westbrook et al. | .......... | 600/529 |
| 2002/0099295 A1 * | 7/2002 | Gil et al. | ...................... | 600/476 |
| 2004/0039270 A1 * | 2/2004 | Keller et al. | ................. | 600/322 |
| 2004/0054290 A1 * | 3/2004 | Chance | ........................ | 600/473 |
| 2005/0189861 A1 * | 9/2005 | Yoshinaga et al. | .......... | 313/440 |
| 2005/0277818 A1 * | 12/2005 | Myers | ......................... | 600/323 |
| 2006/0173257 A1 * | 8/2006 | Nagai et al. | ................. | 600/323 |

OTHER PUBLICATIONS

Brazy, Jane E. et al., "Noninvasive Monitoring of Cerebral Oxygenation in Preterm Infants: Preliminary Observations," *Pediatrics*, Vo. 75, No. 2, pp. 217-225, 1985.
Boushel, R. et al., "Monitoring availability with near infrared spectroscopy (NIRS) in health and disease," *Scandinavian Journal of Medicine and Science in Sports*, vol. 11, pp. 213-222, 2001.
Chapman, K. R., et al., "Range of Accuracy of Two Wavelength Oximetry," *Chest* vol. 89, No. 4, pp. 540-542, 1986.

(Continued)

*Primary Examiner*—Robert L Nasser
*Assistant Examiner*—Karen E Toth
(74) *Attorney, Agent, or Firm*—Steptoe & Johnson LLP

(57) ABSTRACT

A respiratory monitoring apparatus that detects changes in physiological parameters relevant to respiration, including blood oxygen and blood volume, using near infrared spectroscopy. Methods for diagnosing respiratory-related events including hypoxia index, hypopnea, arousal, tissue oxygen debt, and respiratory muscle events or distinguishing central from obstructive sleep apnea are also disclosed.

31 Claims, 19 Drawing Sheets

OTHER PUBLICATIONS

Davies, S. W. et al., "Abnormal diastolic filling patterns in chronic heart failure—relationship to exercise capacity," *European Heart Journal*, vol. 13, pp. 749-757, 1992.

Dyer, John R., "Infrared Spectroscopy," *Application of Absorption Spectroscopy of Organic Compounds*, published by Prentice-Hall Inc., New Jersey, Foundations of Modern Organic Chemistry series, Chap. 3, pp. 22-57, 1965.

Editorial, "Sleep Apnea—A major public health problem," *N. Engl. J. Med.*, vol. 328, pp. 1271-1273, 1993.

Falke, K. J., "Therapeutic Thresholds for Acute Changes in Arterial $O_2$ Partial Pressure," *The Oxygen Status of Arterial Blood*, edited by Zander and Mertzlufft, Karger, Basel, pp. 63-71, 1991.

Ferrari, Marco, et al., "Noninvasive determination of hemoglobin saturation in dogs by derivative near-infrared spectroscopy," *Am. J. Physiol.* 256 (*Heart Circ. Phsiol.* 25) pp. H1493-H1499, 1989.

Ferrari, M, et al., "Principles, techniques, and limitations of near infrared spectroscopy," *Pub. Med., Can. J. Appl. Physiol.*, vol. 4, pp. 463-487, 2004.

Ferrari, Marco, et al., "Effects of graded hypotension on cerebral blood flow, blood volume, and mean transit time in dogs," *Am. J. Physiol.* 262 (*Heart Circ. Physiol.* 31) pp. H1908-H1914, 1992.

Gagnadoux, Frédéric, MD, et al., "Home Unattended vs Hospital Telemonitored Polysomnography in Suspected Obstructive Sleep Apnea Syndrome," *Chest*, vol. 121, pp. 753-758, 2002.

Guilleminault, Christian, MD, et al., "Cardiac Arrhythmia and Conduction Disturbances During Sleep in 400 Patients with Sleep Apnea Syndrome," *Am. J. Cardio.*, vol. 52, pp. 490-494, 1983.

Grace, R.F., "Pulse oximetry, Gold standard of false sense of security?," abstract only, *Pub Med., Med. J.Aust.* vol. 160, No. 10, pp. 638-644, 1994.

Hayakawa, T., et al., "Changes in Cerebral Oxygenation and Hernodynamics During Obstructive Sleep Apneas," *Chest*, vol. 109, No. 4, pp. 916-921, 1996.

He, J. et al., "Mortality and apnea index in obstructive sleep apnea. Experience in 385 male patients," abstract only, *Pub. Med., Chest*, vol. 94, No. 1, pp. 9-14, 1988.

Hernández, Lourdes, MD, "Performance of Nasal Prongs in Sleep Studies," *Chest*, vol. 119, No. 2, pp. 442-450, 2001.

Jöbsis, Franz F., "Noninvasive, Infrared Monitoring of Cerebral and Myocardial Oxygen Sufficiency and Circulatory Parameters," *Science*, vol. 198, pp. 1264-1267, 1977.

Le Bon, Oliver, et al., "Mild to Moderate Sleep Respiratory Events," *Chest*, vol. 118, No. 2, pp. 353-359, 2000.

Leger, Damien, "The Cost of Sleep-Related Accidents: A Report for the National Commission on Sleep Disorders Research," *Sleep*, vol. 17, No. 1, pp. 84-93, 1994.

Mertzlufft, F. et al., "Non-Invasive Continuous Measurement of Arterial Partial $O_2$ Saturation: Pulse Oxymetry," *The Oxygen Status of Arterial Blood*, edited by Zander and Mertzlufft, Pub. Karger, pp. 106-123, 1991.

Sevick, E. M. et al., "Quantitation of Time-and Frequency-Resolved Optical Spectra for the Determination of Tissue Oxygenation," *Analytical Biochemistry*, vol. 195, pp. 330-351, 1991.

Severinghaus, John W. MD et al., "Accuracy of Response of Six Pulse Oximeters to Profound Hypoxia," *Anesthesiology*, vol. 67, pp. 551-558, 1987.

Wahr, Joyce A. et al., "Near-Infrared Spectroscopy: Theory and Applications," *Journal of Cardiothoracic and Vascular Anesthesia*, vol. 10, No. 3, pp. 405-418, 1996.

Wilson, John R. MD et al., "Noninvasive Detection of Skeletal Muscle Underperfusion With Near-Infrared Spectroscopy in Patients With Heart Failure," *Circulation*, vol. 80, No. 6, pp. 1668-1674, 1989.

Young, Terry et al., "The Occurrence of Sleep-Disordered Breathing among Middle-Aged Adults," *New England Journal of Medicine*, vol. 328, pp. 1230-1235, 1993.

Zafar, Subooha MD et al., "Choice of Oximeter Affects Apnea-Hypopnea Index," *Chest*, vol. 127, pp. 80-88, 2005.

\* cited by examiner

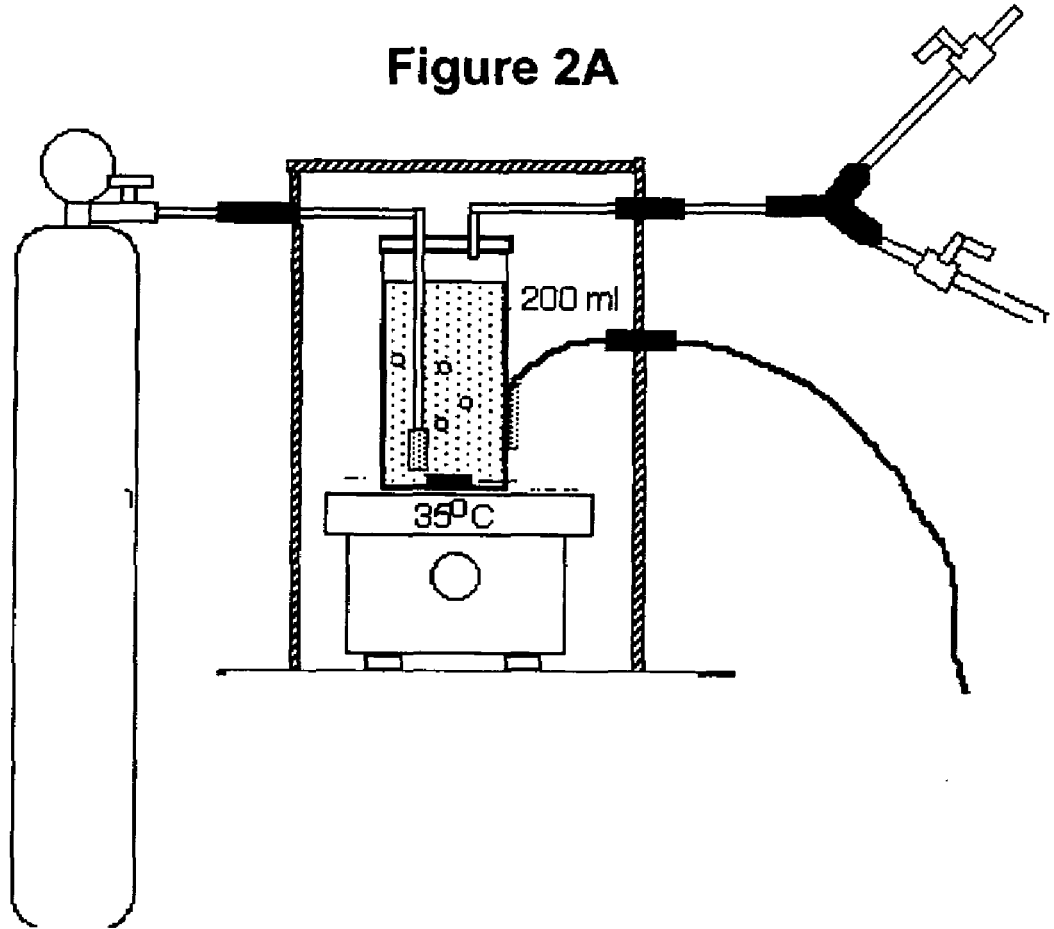

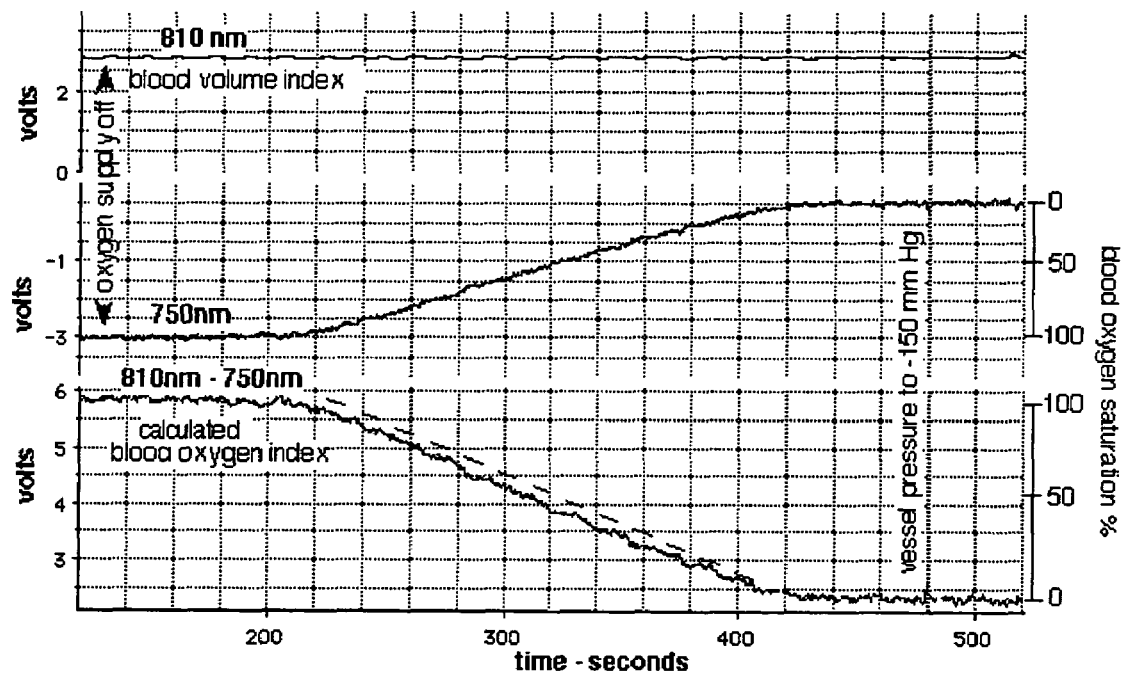

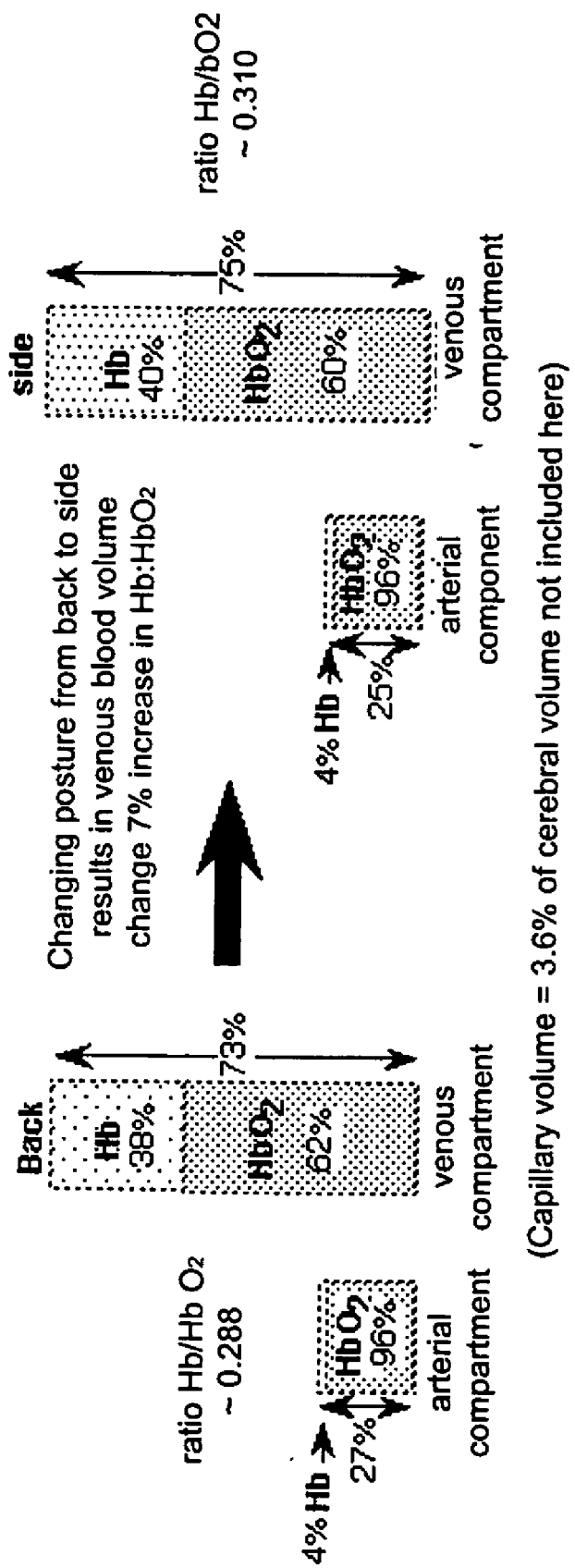

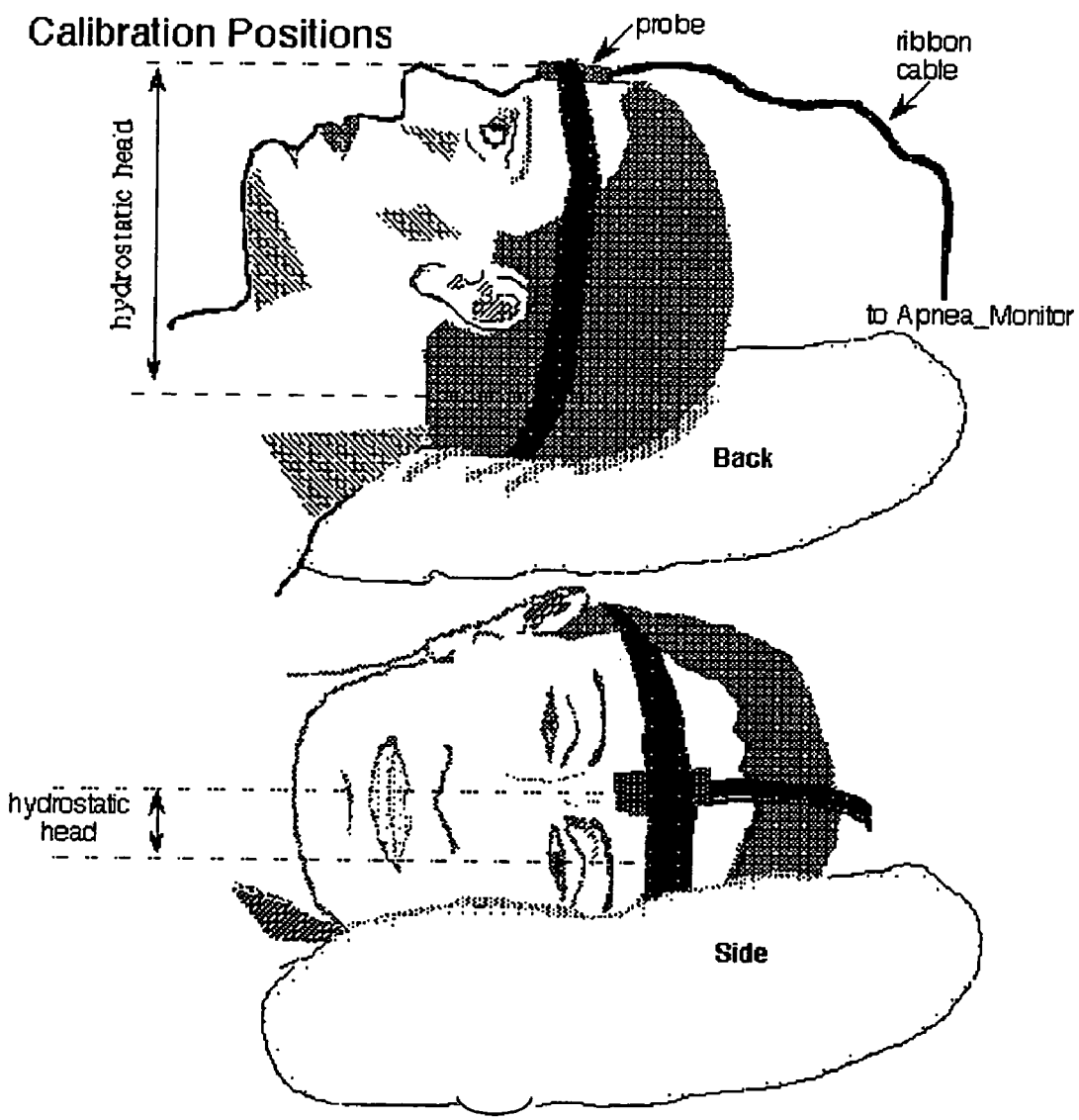

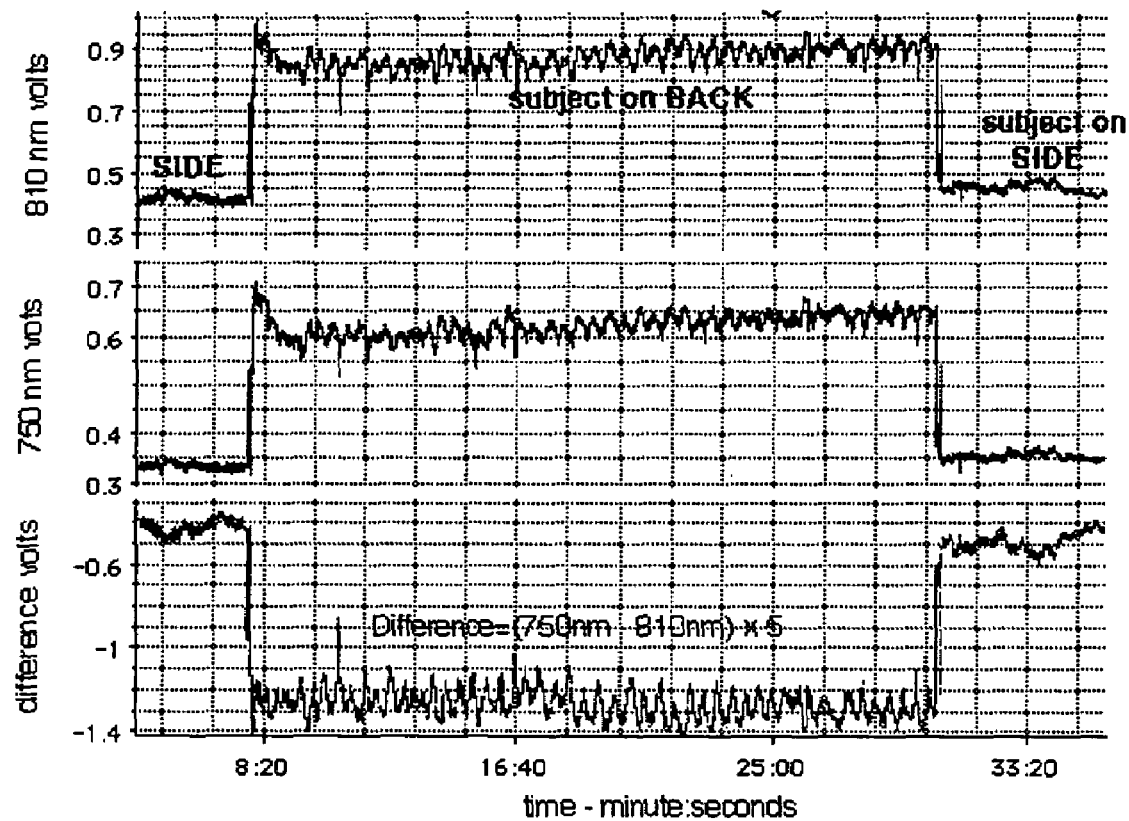

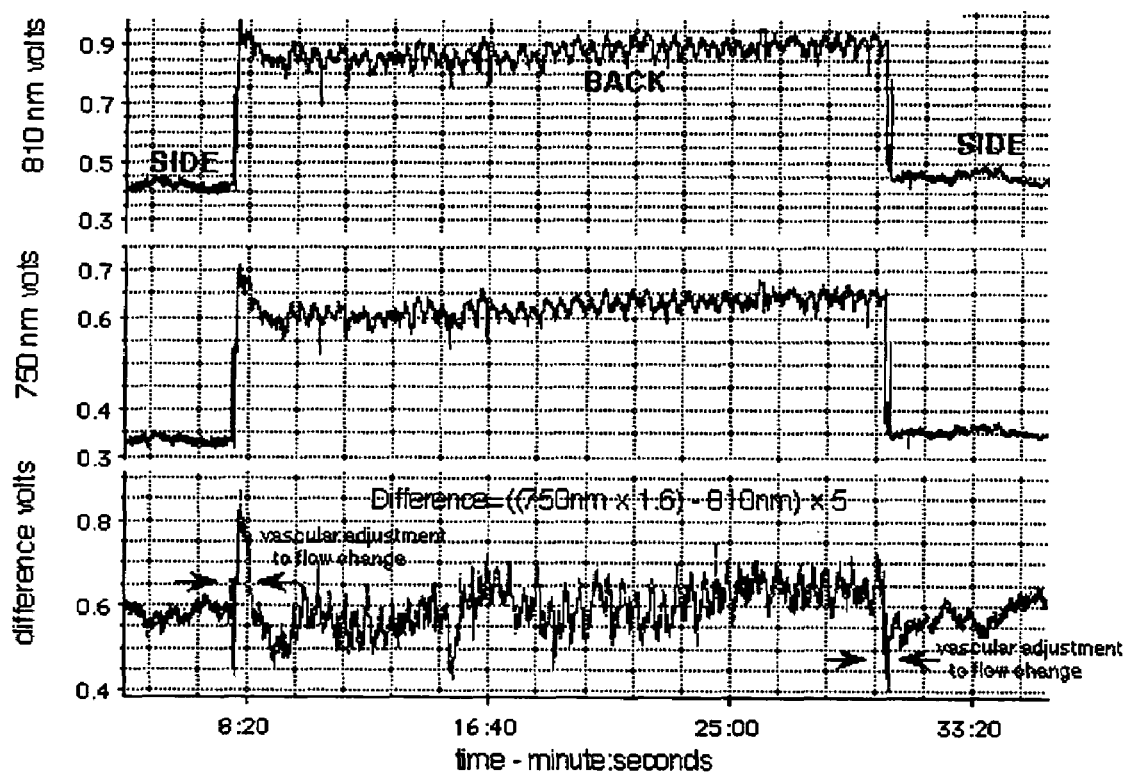

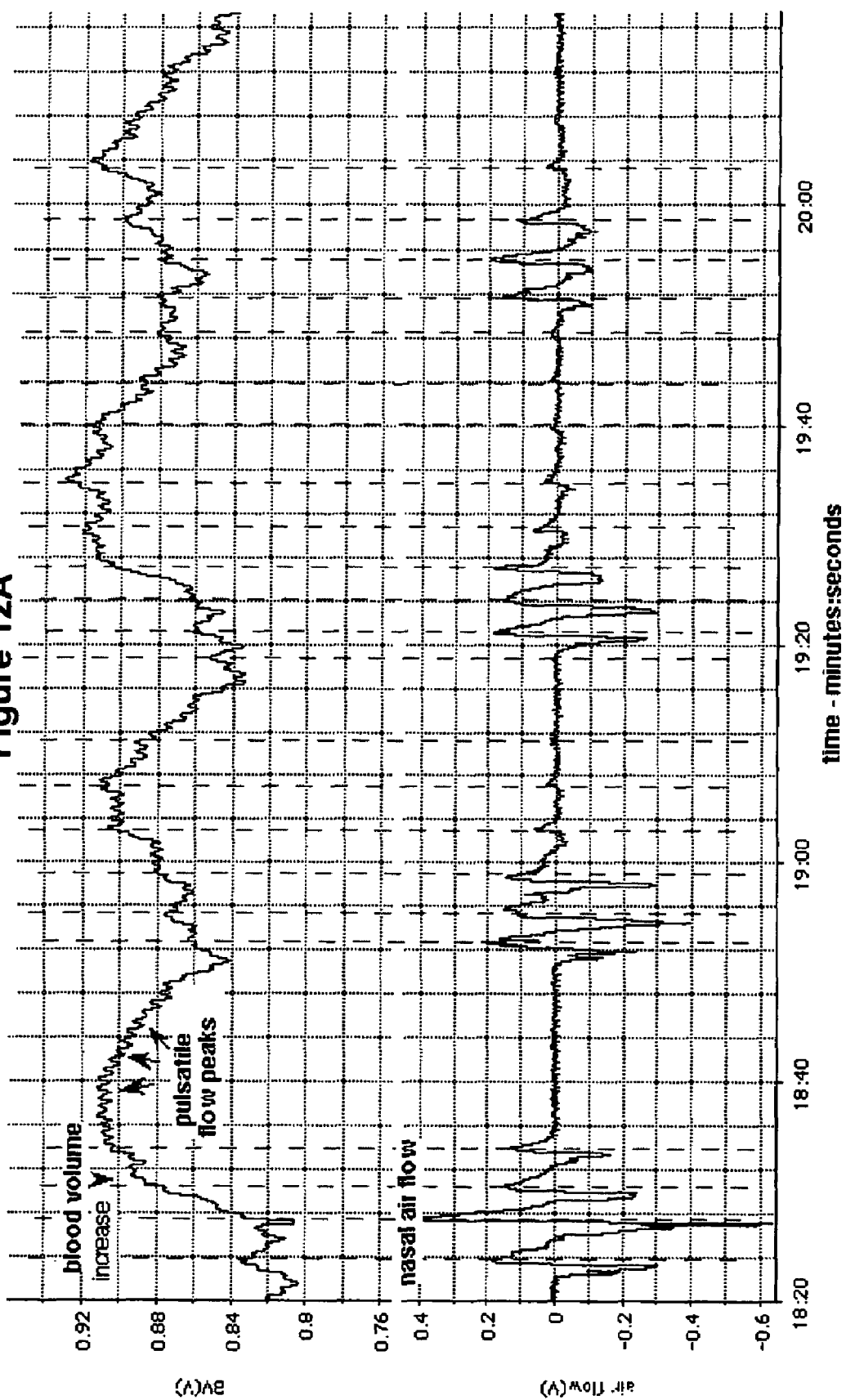

METHODS AND APPARATUS FOR PATIENT MONITORING

The present application claims the benefit of provisional application Ser. No. 60/558,364, filed Mar. 30, 2004, the disclosure of which is expressly incorporated by reference herein in its entirety.

FIELD OF THE INVENTION

The present invention relates generally to medical devices that provide information regarding respiratory parameters.

BACKGROUND OF THE INVENTION

Respiratory monitoring is a crucial tool for clinical diagnostics and patient safety, particularly when a subject is unconscious, such as during sleep or an induced unconscious state.

In the current diagnosis of disordered respiration, such as sleep apnea, extensive instrumentation is required. Techniques and devices used for diagnosing sleep apnea include electroencephalograms, electrocardiograms, electromyographs, pulse oximetry, ocular and body movement strain gauges, snoring recording, postural position monitoring and respiratory gas flow monitoring. In practice, only four or so of these transducers will be attached in most sleep clinics.

Nasal airflow (or pressure) transducers are generally used to provide the main signal for apnea/hypoapnea scoring, although pulse oximetry (as a measure of arterial blood-oxygen) and electroencephalography (as a measure of arousal) are used as confirmatory information. Linear displacement transducers may be used for detecting chest and abdomen expansion as a measure of respiration and sound (snoring) levels recorded. Some of these transducers have been modified for home monitoring, thus reducing costs associated with sleep clinical diagnostics, however, technical assistance at set up is still recommended based on studies comparing user or technician monitoring set up (Gaqnadoux and Pelletier-Fleury, Chest (March) 2002).

The signal derived from the transducer provides a trace showing the inhalation/exhalation cycle, and time periods of no respiratory activity. It is also useful in estimating periods of insufficient respiration, such as those characteristic of hypopnea (Hemdndez et al., Chest 2001; 119:442-450), although confirmatory evidence is generally needed for the latter, either oxygen desaturation (pulse oximeter) or else arousal (usually EEG or accelerometer) or both.

There are several causes of sleep apnea. Obstructive sleep apnea (OSA) is the more common form, characterised by the soft palette blocking the air passage. During OSA, diaphragm movement persists in respiratory effort. This does not occur with central sleep apnea, where breathing stops due to lack of respiratory muscle effort induced by lack of cerebral signal for respiratory muscle contraction. Mixed sleep apnea results when both of these effects occur.

During mouth breathing, nasal prongs give false positive apnea events, and generally the signal is poor during periods of snoring, a parameter which in itself is characteristic of sleep apnea. However, monitoring snoring as a diagnostic parameter has limited diagnostic value unless used in conjunction with other transducers (Hemdndez et al., Chest 2001; 119:442-450).

Pulse oximetry is universally used to monitor blood-oxygen saturation in patients during respiratory studies. The pulse oximeter probe is designed for clamping to a finger, and provides a measure of the arterial blood-oxygen saturation level mainly in the skin. There are several disadvantages in using oximetry for measuring hypoxia, including:

1) The skin (finger) is a low metabolizing tissue that is unlikely to reflect the oxygen saturation changes experienced by high metabolizing organs, particularly the heart and brain.
2) The finger attachment is not appropriate for use on subjects who thrash around during the study, as a consequence of continual arousal (dislodgment of the oximeter probe is one of the most common equipment failures in respiratory monitoring). Body movement leads to changes in baseline referred to as movement artefact, which can be inaccurately interpreted as desaturation events. Tightly clamping probes, which can reduce this movement artefact, tends to be uncomfortable when used for long periods.
3) The accuracy of pulse oximetry at low blood-oxygen saturation levels has been called into question by investigators (Mertzluffi and Zander, (1991); In the Oxygen Status of Arterial Blood. Ed. Zander R. and Mertzlufft F., Publ. Karger, N.Y., p 106-123).
4) The pulse-oximeter depends on pulsatile blood flow for timing in sampling. During hypoxia, pulsatile flow can be difficult to pick up in the skin due to tissue capillary-bed bypassing of the blood in the skin, via arteriolar-venular shunts, when oxygenated blood is diverted to increase critical tissue perfusion.

A positive diagnosis of sleep apnea is generally made if the instruments recording signals indicate five or more apnea events per hour (each exceeding 10 seconds) during sleep. An excess of 30 apneas per hour is usually required for a clinical diagnosis of severe sleep apnea. Many clinics also include hypoapnea scoring (insufficient respiratory rates for >2 minutes) based on respiratory airflow data and/or the number of arousal's recorded per hour.

Diagnostic scoring can be ambiguous for milder to moderate sleep-apnea conditions, with some clinicians recommending studies over two nights to reduce false positive/negative diagnosis (Le Bon et al., Chest (August) 2000). The high cost of sleep clinic studies, and the number of possible candidates to be screened, means that screening of all patients requiring this extended testing is not cost effective, and thus often not feasible.

A number of biomolecules absorb near infrared radiation at specific wavelengths via bond stretching or dipole interactions, and this property is utilised by near infrared spectroscopy (NIRS) (Dyer, (1965) pp. 22-57, Pub. Prentice-Hall Inc. New Jersey). Like oximetry, NIRS detects photons at two or more wavelengths that have been scattered through tissue. The flux densities of the emerging photons (at 750 nm and 810 nm), are proportional to the ratio of deoxyhemoglobin:oxyhemoglobin within the tissue, and can be used to calculate the physiological parameter of blood hemoglobin oxygen saturation.

NIRS methodology differs from pulse oximetry in two important respects:
(1) Pulse oximetry relies in part on visible radiation, usually at 660 nm, which limits photon penetration to several millimeters travel through tissue, whereas near infrared radiation has significantly greater penetration;
(2) NIRS is optimized to measure deoxyhemoglobin proportions, whereas pulse oximetry which is optimized to measure oxyhemoglobin levels.

The low penetration depth of the radiation used in pulse oximetry (less than 10 mm at a wavelength of ~660 nm), means it is unsuitable for non-invasive deep tissue blood-oxygen assessment. In contrast, a device using NIR-radiation only can readily penetrate bone and assess deep tissue.

SUMMARY OF THE INVENTION

The present invention relates to methods and devices for monitoring or diagnosing disordered respiration in a patient.

In a first broad form, the invention provides a method of detecting disordered respiration in a patient, the method comprising:
(a) exposing the patient's cerebral tissue to radiation, the radiation having at least first and second predetermined wavelengths, the first and second predetermined wavelengths being between about 730 nm to 770 nm, and 790 nm to 830 nm respectively;
(b) sensing the levels of radiation reflected by the cerebral tissue at the first and second predetermined wavelengths;
(c) in a calibration step:
 (i) determining reflection levels for first and second patient orientations; and,
 (ii) using the determined reflection levels to determine a calibration factor; and
(d) in a monitoring step:
 (i) calculating a blood oxygen index in accordance with the sensed reflected radiation and the calibration factor; and,
 (ii) detecting a presence or absence of disordered respiration in the patient based at least in part on changes in the blood oxygen index determined in accordance with the calibration factor.

Preferably, the disordered respiration is a sleep-related respiratory deregulation and in a particularly preferred form, is obstructive sleep apnea, central sleep apnea or both.

Preferably, the first and second patient orientations include:
(e) the patient lying on their back; and,
(f) the patient lying on their side.

In a further preferred form, the blood oxygen index is determined in accordance with the equation:

$$|B-A|$$

wherein:
A is the reflected level at the first predetermined frequency; and,
B is the reflected level at the second predetermined frequency.

In a preferred embodiment, the blood oxygen index is determined in accordance with one of the following equations:

$$|B-kA| \text{ or } [Ak-B]$$

wherein:
k is the calibration factor.

Preferably, the calibration factor is determined empirically so as to reduce effects of hydrostatic head change effect on the blood oxygen index.

Preferably, the method includes using first and second light-emitting diodes (LEDs) to generate the first and second wavelengths respectively.

Also preferably, the method includes using a photodiode to sense the absorbed radiation.

In a further preferred form, the method includes:
a) selectively exposing the patient's cerebral tissue to radiation;
b) sensing reflected radiation when the patient's cerebral tissue is exposed, to determine an exposed level;
c) sensing radiation when the patient's cerebral tissue is not exposed to determine an ambient radiation level; and,
d) determining a reflected level by subtracting the ambient radiation level from the exposed level.

Preferably, the reflected values for the first and second wavelengths and ambient light are consecutively sampled at least 30 times per second.

In a further preferred form, the method includes using algorithms to calculate parameters selected from the group consisting of oxygen debt accumulation value during insufficient respiration, hypoxic value of apnea events, pulsatile flow, blood volume cycling, diaphragm movements during respiration patient wherein a movement is indicative of obstructive, central or mixed type sleep apnea, arousals during an unconscious state and recovery time to quiescent saturation.

Preferably, the method includes performing the monitoring step for a predetermined time period.

In a further form, the invention relates to a method of monitoring flow response times to hydrostatic pressure adjustments in a patient, the method comprising:
(a) exposing the patient's cerebral tissue to radiation, the radiation having at least first and second predetermined wavelengths, the first and second predetermined wavelengths being between about 730 nm to 770 nm, and 790 nm to 830 nm respectively;
(b) sensing the levels of radiation absorbed by the cerebral tissue at the first and second predetermined wavelengths;
(c) in a calibration step:
 (i) determining absorption levels for first and second patient orientations; and,
 (ii) using the determined absorption levels to determine a calibration factor; and
(d) in a monitoring step:
 (i) calculating a blood oxygen index in accordance with the sensed absorbed radiation and the calibration factor; and, detecting a flow response time to a hydrostatic pressure adjustment in the patient based at least in part on changes in the blood oxygen index determined in accordance with the calibration factor.

In another broad form, the invention relates to an apparatus for detecting disordered respiration or a flow response time to a hydrostatic pressure adjustment in a patient, the apparatus comprising:
(a) a radiation source for exposing the patient's cerebral tissue to radiation, the radiation having at least first and second predetermined wavelengths, the first and second predetermined wavelengths being between about 730 nm to 770 nm, and 790 nm to 830 nm respectively;
(b) a sensor for sensing the level of radiation reflected by the cerebral tissue at the first and second predetermined wavelengths; and,
(c) a processor for:
 (i) in a calibration step:
  (a) determining reflected radiation levels for first and second patient orientations; and,
  (b) using the determined absorption levels to determine a calibration factor; and
 (ii) in a monitoring step:
  (a) calculating a blood oxygen index in accordance with the sensed absorbed radiation and the calibration factor; and,
  (b) detecting a presence or absence of disordered respiration in the patient based at least in part on changes in the blood oxygen index determined in accordance with the calibration factor.

Preferably, the radiation source includes first and second LEDs for generating the first and second predetermined wavelengths respectively.

Preferably, the sensor includes a photodiode for sensing the reflected radiation.

In another preferred form, the apparatus includes controller for controlling the operation of the radiation source and the sensor.

Even more preferably, the controller is adapted to:
(a) selectively activate the radiation source to thereby expose the patient's cerebral tissue to radiation;
(b) selectively sample signals from the sensor to thereby sense radiation when:
  (i) the patient's cerebral tissue is exposed to determine an exposed radiation level;
  (ii) the patient's cerebral tissue is not exposed to determine an ambient radiation level; and,
(c) determine a reflected level by subtracting the ambient level from the exposed level.

Preferably, the controller is adapted to cause reflected values for the first and second wavelengths and ambient light to be consecutively sampled at least 30 times per second.

Also preferably, the controller includes:
(a) a processor for controlling the radiation source and the sampling time interval of the sensor; and,
(b) a memory for storing reflected level signal values.

Preferably, the processor is adapted to control a pulsed radiation source, and even more preferably, a sampling time interval of the sensor.

In another preferred form, the processor is adapted to perform at least some processing of the reflected level signals.

Preferably, the controller includes a communication means for transferring data to a remote processing system, the remote processing system being adapted to perform at least some processing of the reflected level.

Even more preferably, the remote processing system is adapted to display a reflected level.

In a preferred form, the apparatus includes a user input for controlling the controller.

Preferably, the user input is used for selectively activating at least one of the calibration step and the monitoring step.

Even more preferably, the controller is provided in a housing.

In a particularly preferred form, the housing is suitable for home use by a patient.

Preferably, the radiation source and the sensor are provided in a probe coupled to the housing, the probe being adapted for attachment to the patient in use.

In a particularly preferred form, the probe is formed from silicon rubber.

In another form, the apparatus is adapted to perform the methods of the invention.

BRIEF DESCRIPTION OF THE DRAWINGS

FIG. 2A illustrates an example of experimental conditions suitable for testing response of the respiratory monitor to changes in blood oxygen in vitro;

FIG. 2B is a graphical representation of sample traces for a solution of 5% hematocrit, showing voltage level at 750 nm, 810 nm and a calculated blood oxygen index;

FIG. 4 is a schematic diagram illustrating changes in blood oxygenation measure caused by a postural change;

FIG. 5A is a schematic diagram showing a sample patient calibration step of a preferred device of the invention;

FIG. 6A is a graphical representation of respiratory-related parameters obtained by an apparatus according to an embodiment of the invention;

FIG. 6B is a graphical representation of respiratory-related parameters obtained by an apparatus according to an embodiment of the invention;

FIG. 12A is a graphical representation of phase relationship between respiratory airflow, blood volume and blood hydrostatic head changes;

DETAILED DESCRIPTION OF THE PREFERRED EMBODIMENTS

Figure 1:
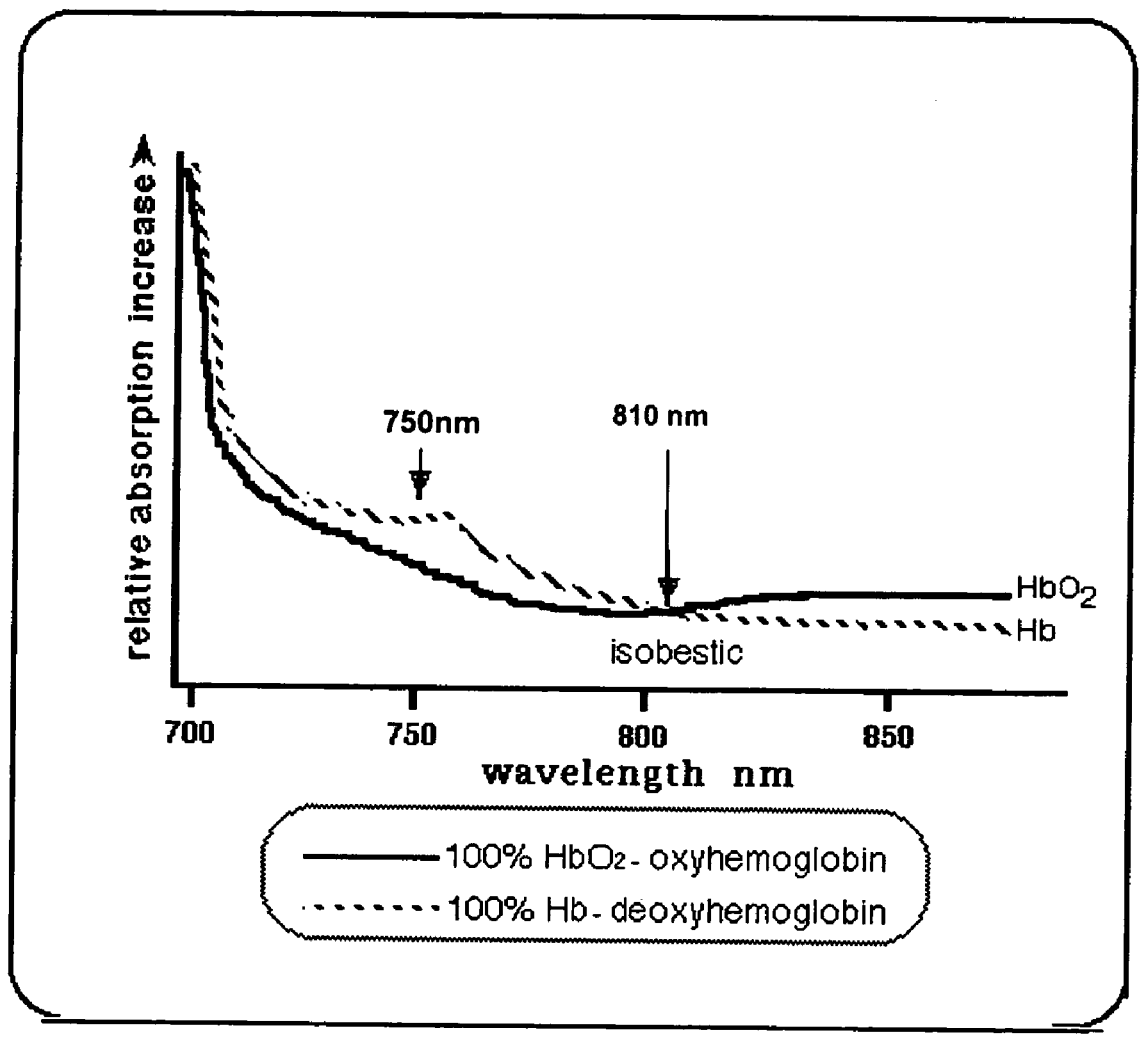
FIG. 1 is a graphical representation of a spectral scan of whole blood in a near infrared range.

The present invention involves apparatus and methods, for the diagnosis or monitoring of disordered respiratory regulation or flow response time to hydrostatic pressure adjustment in a patient.

An example of apparatus suitable for detecting sleep apnoea will now be described with reference to FIG. 3A.

In particular, the apparatus is adapted to perform near infra-red spectroscopy (NIRS) and is therefore typically formed from a processing system 10 coupled to suitable radiation sources 11, 12, a detector 13, and an amplifier 14. In one example, the processing system 10 is formed from a microprocessor 20, a memory 21, and an external interface 24, coupled together via a bus 23. In this case, the radiation sources 11, 12 and the amplifier 14 are coupled to the external interface 24 as shown.

In use, the radiation sources 11, 12 are adapted to generate near infra-red radiation at respective predetermined wavelengths, with the radiation being detected by the detector 13. The output from the detector 13 is amplified and sampled by the amplifier, which therefore typically includes an analogue-to-digital converter, to provide a digital signal to the processing system 10.

This is typically achieved by utilising two near infra-red light emitting diodes (LEDs) adapted to emit radiation at approximately 750 nm and 810 nm respectively. The detector 13 is typically a photodiode adapted to detect radiation at these wavelengths, which may be achieved through the use of a standard photodiode and an appropriate bandpass filter, as will be appreciated by persons skilled in the art.

The processing system 10 is adapted to control the operation of the LEDs 11, 12, the detector 13 and the amplifier 14, as well as to store and optionally process any sampled signals. Accordingly, the processing system may be any form of processing system provided with suitable applications software and a suitable external interface. Thus the processing system may be formed from a suitably programmed personal computer, lap-top, palm-top, PDA, mobile phone, or the like, or may be implemented using a suitable custom hardware configuration, as will be described in more detail below.

In operation, the processing system is adapted to selectively activate the radiation sources 11, 12 in accordance with a predetermined pulse sequence. This is typically performed such that each radiation source 11, 12 is activated at a respective time, with signals from the detector 13 being sampled at times to coincide with times at which the radiation sources 11, 12 are activated. An example of a suitable pulse sequence is shown in FIG. 3B. Additional sampling may also be performed at times during which the radiation sources 11, 12 are not active to thereby allow ambient radiation levels only to be detected. The signals caused by ambient radiation levels alone can then be subtracted from signals detected during activation of the LEDs, to thereby allow the effects of ambient radiation to be accounted for.

It will be appreciated from that person skilled in the art that the device may be formed on specialised hardware or the like. In one example, shown in FIG. 3C, the device includes a probe 30 containing the LEDs 11, 12, the photodiode 13 and the supporting electronics such as the amplifier 14. The probe 30 is typically formed by having the LEDs 11, 12 and the detector being embedded in soft silicon rubber. In one example the size of the probe 30 is approximately 50 mm×20 mm×10 mm. Suitably, the shape of the probe is fashioned to conform to the surface topography of the forehead, to minimise ambient radiation access to the sensor, or prevent dislogement with rapid head movement. Electronic components can be incorporated into the probe by any suitable technique, such as by first coating in high resistive silicon rubber, then mixing the remaining silicon with a carbon filler (black) to eliminate ambient light accessing the photodiode.

In this example, the photodiode is coupled to an electrometer amplifier 14 whose external signal input terminals are impedance matched to the photodiode to reduce the photodiode's capacitive load, and thereby improve response time to signal changes. The amplifier 14 also functions as a current-to-voltage converter plus amplifier (gain=1000) providing a proportional conversion to a voltage from the photon flux reaching the photodiode.

The probe is coupled to a housing 31 via a 2 meter flexible polypropylene 6-core ribbon cable 32. The housing 31 houses the processing system 10, and an associated power source, such as a battery, and is provided with a number of input and output devices including an on/off switch 33, a calibration switch 34, and three visual indicators 35, 36 and 37.

Figure 5B:
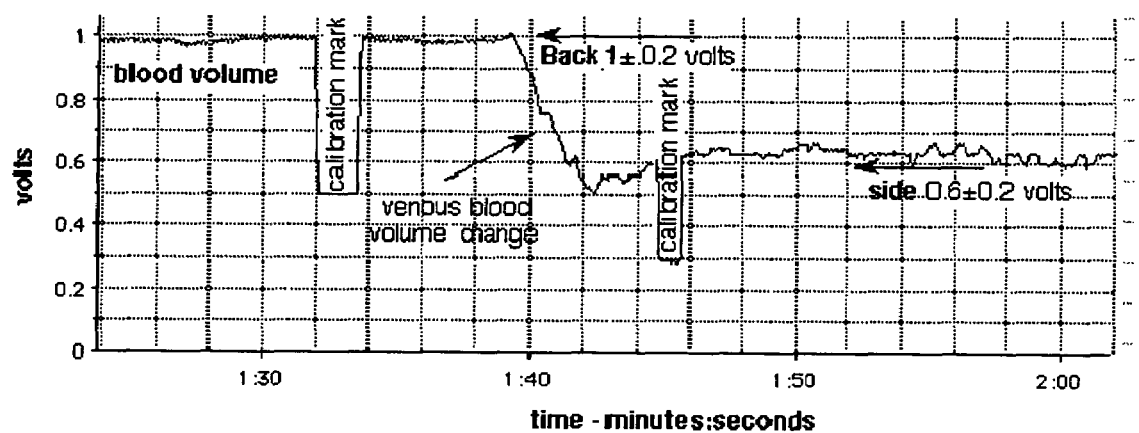
FIG. 5B is a graphical representation of the data generated by the sample patient calibration step of FIG. 5A.

In use, activation of the on/off switch 33 causes power to be supplied to the processing system allowing the system to be activated. In general, this also triggers the LEDs 11, 12 and the detector 13, thereby causing measurements to be made. The indicating devices 35, 36, which are typically LEDs are utilised to indicate mark signal levels of the orientation of the patient whilst an indicating device 37 is used to indicate whether the device is active. Finally, the calibration switch 34 is used to cause the device to be calibrated. The LEDs, 35, 36, are illuminated when the device is turned on via the on/off switch 33. When the patient is lying on their back, the calibration switch, 34, is pressed. This action extinguishes indicating device 35, suitably providing a specific voltage to be recorded within a blood volume signal which provides a mark for the blood volume level present when the patient is on their back. Similarly, the patient then lies on their side and the calibration button, 34, is again pressed so that device 35 is extinguished and a specific voltage included with the blood volume signal to indicate blood volume level expected when the patient is lying on their side. The graphical representation of these calibration steps are shown in FIG. 5B. The calibration is complete when both LEDs 35 and 36 extinguished.

In one example, the probe 30 also include a ground plate, which in use is in contact with the patient's skin, thereby reducing AC-line pickup.

Once the device is activated, by turning on the on/off switch 33, sampling of signals from the photodiode 13 will begin immediately. In this example, the signals from the photodiode 13 are amplified by the amplifier 14, before being transferred to the processing system 10, where the signals undergo 10-bit analogue-to-digital conversion by the processor 20. Signals for each wavelength plus ambient light are consecutively sampled at 50-times per second, with the ambient light signal voltage being subtracted from each NIR-LED signal voltage. An indication of the signal voltage is stored in the memory 21, which may be a Flash-RAM memory module, or the like.

The stored data can then be subsequently transferred to a remote system, such as PC, for analysis. In one example, this is achieved using a USB port 38, although it will be appreciated that this could also be achieved by wireless communication between the processing system 10, and the remote system, or by removal and physical transfer of the memory 22, for example if the memory 22 is provided on removable media.

In this case, the data is transferred to a remote system for analysis. However, it is also possible for the processing system 10 to perform initial analysis of the result, with an indication being provided by a suitable output. For example, the stored signal would be processed to identify events within physiological parameters, such as a peak-to-peak time for a pulsatile flow, respiration ratess, blood flow cycling with hypopnea and voltage transitions characteristic of arousal peaks in the blood volume signal. Analysis simultaneous transitions in blood volume and blood oxygen transitions may be used for characterising apnea events. Deregulation in a respiratory parameter could then suitably be displayed to an inbuilt LCD screen, or be used to set off an alarm.

Figure 3A:
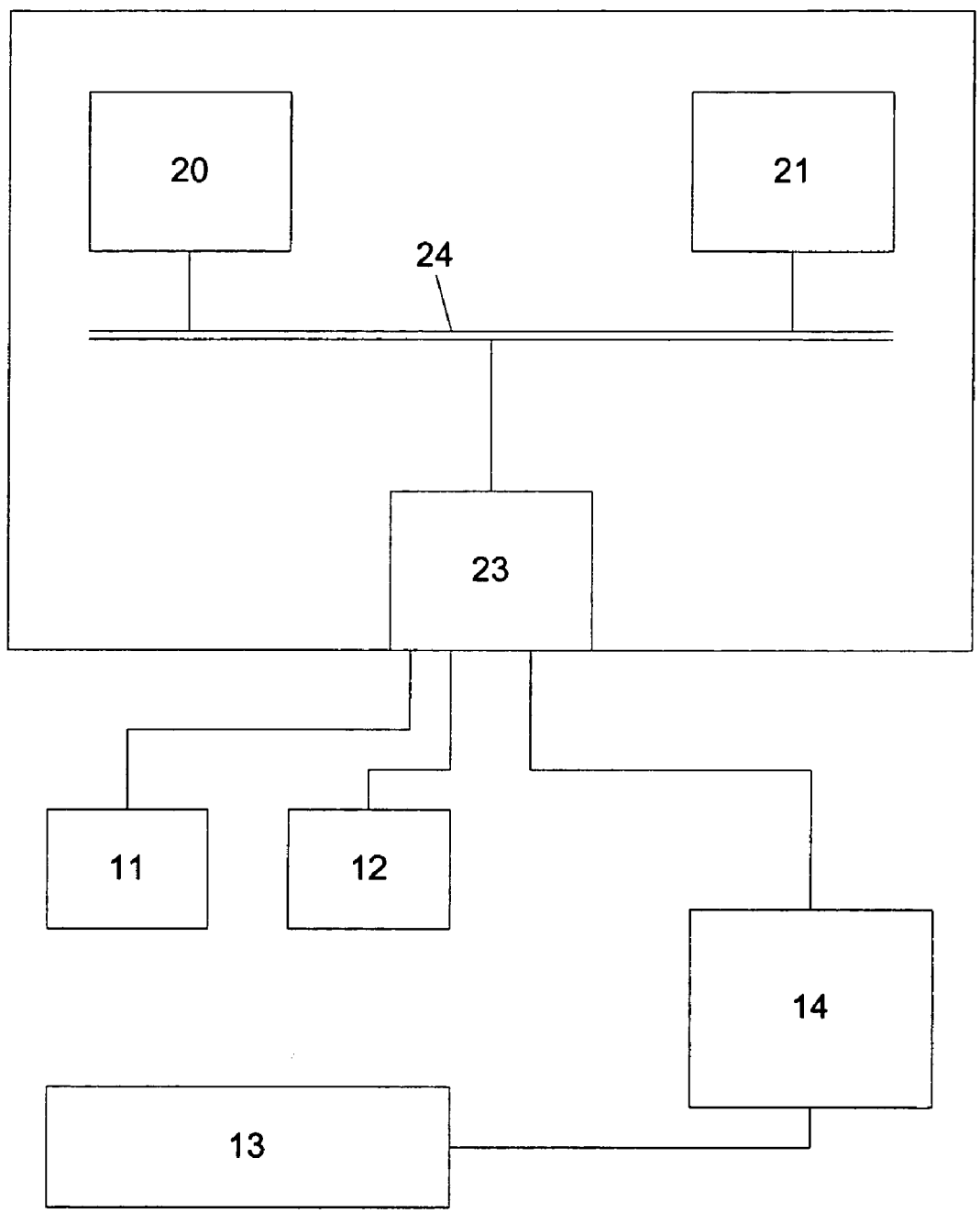
FIG. 3A is a schematic representation of an apparatus according to an embodiment of the invention.
Figure 3B:
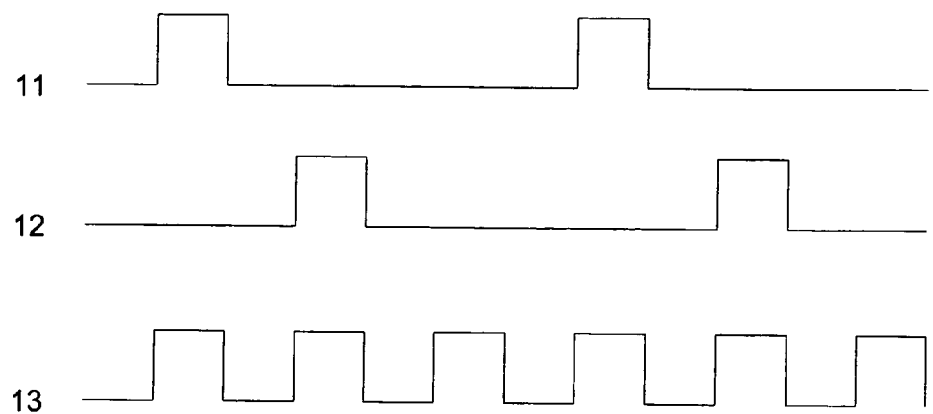
FIG. 3B is a schematic representation of a pulse sequence for components in the apparatus of the invention.
Figure 3C:
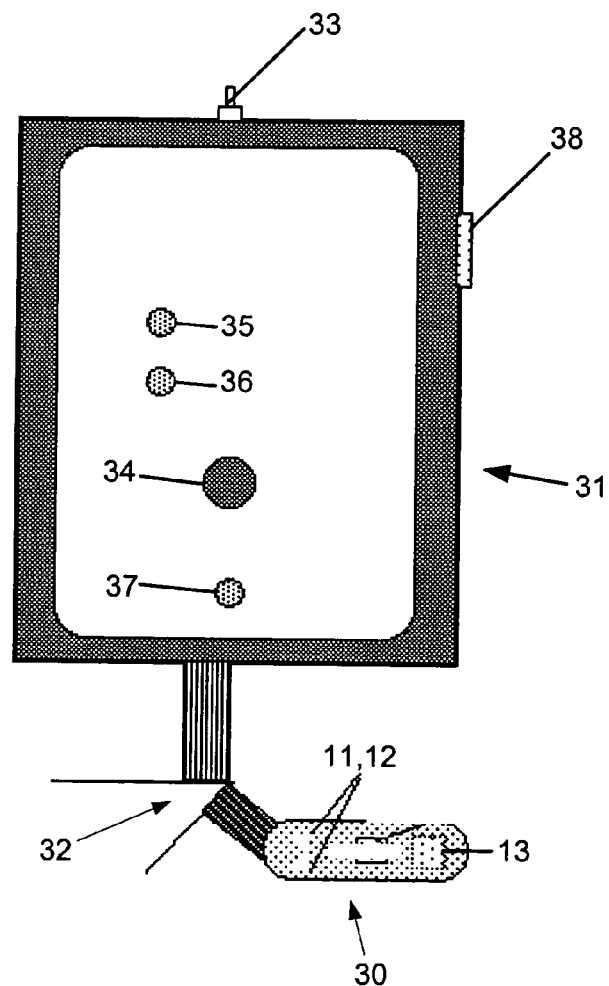
FIG. 3C is a schematic illustration of an apparatus according to a preferred embodiment of the invention.

Physiological events can be obtained for use in the methods of the invention using an apparatus shown in FIG. 3C, where the sensor can be formed as a probe which is placed centrally on the forehead, and secured, such as by way of an adjustable elastic strap, on the central axis of body rotation of a patient. As mentioned, the probe can be attached to the device via a flexible ribbon cable which allows maximum body movement without dislodgment.

The trace in FIG. 5B shows a subject's blood volume increase invoked by postural change. With decreased (negative) hydrostatic head, a subject's blood concentration increases in the tissue being interrogated, and fewer photons manage to pass through the tissue, hence the signal level drops. The signal values for these different postural positions are marked on the trace in FIG. 5B during the calibration. These values will be different for each subject, depending on attenuation differences such as skull thickness.

Accordingly, it is preferred that for each patient, the device's calibration set up is needed (provides the trace's calibration mark) while the subject is in each postural position. The values measured can then be used to track postural changes during a monitoring or diagnostic study. Preferably, the trace obtained during such a study can be used to infer other postures. Using the trace in FIG. 5B as an illustration, if the signal plateaus above 1.2 volts then the subject has increased pillow height or if a large signal shift, more likely to a sitting position. A signal plateau below 0.58 volts for this patient may indicate lower head height, consequent to, for example, reduced pillow height. A semi-circular movement in the trace may be consistent with an 180° roll over.

Signal level movements correlating with postural changes usually result in changes in the blood-oxygen signal. These shifts are not due to metabolic changes but rather changes in deoxyhemoglobin:oxyhemoglobin (Hb/HbO2) proportions. Unlike the arterial circulation, which is maintained within a pressurised range, blood pressure in the veins is close to atmospheric pressure. The extent of venous blood engorgement within a tissue is dependent on the hydrostatic venous blood pressure head in the tissue relative to height above (or below) the right atrium. As such, there is sufficient difference in hydrostatic height in a subject lying on their back compared to their side to give a distinct signal level for each supine posture, illustrated in FIG. 5A. The subject's position shows the difference in hydrostatic head with the corresponding representation on the blood volume trace. The reasoning for this change is presented schematically in FIG. 4, where a small movement in venous volume results in a significant change in the Hb:HbO2 ratio (~7%). The movement indicated for arterial volume is likely overstated so that the ratio is likely>7%.

The consequences of the venous blood shift is that body movements can mask real changes in oxygen saturation levels. Much of this interference can be removed by modifying the blood-oxygen algorithm, such as by using the calibration values for 'back' and 'side', by employing a multiplying factor "k" value until the shift in blood-oxygen with posture change is minimized in the trace. FIG. 6 shows a segment from a sleep study in which the subject rolls from their side to their back at which point there were racked, with shallow apneas until again they returned on their side.

FIG. 6A show the signal changes in response to postural shifts. The third trace, blood-oxygen index, 750 nm-810 nm, also shows this change. This algorithm is modified to 750 nm×k-810 nm, where "k" was empirically determined as the value that removed hydrostatic blood changes from the blood-oxygen index trace.

FIG. 6B illustrates sample venous blood hydrostatic changes which have been minimized when k=1.60.

Cerebral blood flow is controlled by arteriole contraction/dilation and hydrostatic head height, assuming constant mean blood pressure. When the hydrostatic head is increased, such as when a subject moves from their side to their back, flow has to readjust. With increased negative hydrostatic head, cerebral flow rate increases until the arteriole's vascular smooth muscle adjusts flow rates back to homeostasis. Accordingly, the rapid transient positive peak in the FIG. 6B provides a response time to homeostasis (~20 sec.). Similarly, as the subject rolls back onto their side a negative peak response (10 seconds) to vascular adjustment is observed.

Flow response times to hydrostatic pressure adjustments have not been monitored non-invasively before, so the potential diagnostic value has not been explored. This apparatus and methods of the invention may thus be applied to explore possible response times as they relate to pathologies.

The apparatus and methods of the invention will now be illustrated by way of the following, non-limiting Examples.

EXAMPLE 1

Use of NIRS for Measuring Physiological Parameters (i) Blood Oxygen Saturation (StO2) Index FIG. 1 illustrates the response of infrared light when transmitted through blood. The relatively low absorption of photons in the infrared part of the spectrum compared to that of the visible part of the spectrum (below 700 nm) is shown, as is an absorption peak centered at ~760 nm evident with deoxygenated blood compared to oxygenated blood (StO2);

Finally, the wavelength at which the light absorption is independent of blood oxygen saturation levels, 810±5 nm, called the isosbestic wavelength, is also marked indicated in FIG. 1.

Above 810 nm, oxyhemoglobin shows a higher absorption than deoxyhemoglobin, the converse occurs below 810 nm.

A percentage of oxygen saturation of the hemoglobin within a tissue of interest can be calculated using NIRS from the following equation:

$$stO2(\%) = 100 - \frac{deoxyhemoglobin \times 100}{deoxyhemoglobin + oxyhemoglobin}$$

The comparison of absorption between wave lengths 760 nm and 8100 nm provides a measure of the proportion of blood in which oxygen is bound to hemoglobin (Hb), ie Hb/(Hb+HbO2) (Sevick et al., (1991) Anal. Biochem. 195: 330-351).

(ii) Blood Volume Signal

Blood volume within a tissue can be quantified using NIRS by measurement of the concentration of hemoglobin or red blood cells within the photon path. Incident photons from NIRS are attenuated due to scattering by tissue, and also by absorption, the latter principally by hemoglobin (Sevick et al., (1991) Anal. Biochem. 195: 330-351). While attenuation due to photon scattering in tissue will be constant (for a given measurement site), hemoglobin absorption will vary as the tissue blood content changes.

Relative blood volume measurements can be obtained from a signal generated from photons at around the isosbestic wavelength of 810 nm, which is independent of changes in tissue hemoglobin oxygenation percentage (StO2) (ie cross talk between oxyhemoglobin-to-deoxyhemoglobin proportions).

While other tissue chromophores can also absorb in the near infrared range, particularly in neural tissue (eg cytochrome C), their effect on signals derived from wavelengths of 810 nm or lower is minimal, relative to the degree of hemoglobin absorption within the tissue.

(iii) Tissue Blood Content (TBC)

Non-invasive blood volume measurements using NIRS can show changes in hemoglobin concentration in the photon path and indirectly, blood flow changes. Hemoglobin is confined to blood vessels, where the red blood-cell concentration of blood or hematocrit (Hct) is generally between 40 to 45% (packed red blood cells/100 ml whole blood). The average hemoglobin concentration distribution within a volume of tissue through which the photons pass will average one tenth or less of this value. For instance the TBC for forebrain ranges between 2 to 5% Hct, (as a proportion of packed red blood cells/100 ml tissue volume). This is similar to blood hematocrit (Hct) except that it applies to whole tissue rather than just blood.

EXAMPLE 2

Device Linearity for the Measurement of Blood-Oxygen

Materials and Methods

FIG. 2A shows experimental conditions for testing the response of the device to changes in blood oxygen experimentally in vitro. The equipment in the top of FIG. 2A shows a method for obtaining a 0 to 100% oxygen saturation in blood (ignoring the likely 1% oxidized hemoglobin) in pH-buffered solutions containing a known concentration of hemoglobin (5%, 4%, 3%, 3%, 2%, 1%, 0.5%, 0%) (in sheep red blood cells). Oxygen is stripped from the hemoglobin via competition with activated aerobic yeast, which consume oxygen in their metabolic activity. Increased/decreased pressures above the solution help confirm that total oxygen saturation/desaturation of the hemoglobin has occurred. The hemoglobin is again oxygen saturated by aspirating fine bubbles of oxygen through the solution for some minutes. One hundred percent blood-oxygen saturation was confirmed by pressurizing the vessel to observe any further uptake of oxygen assess by changes in the 750 nm signal. Tissue scattering properties simulated by the addition of aluminum oxide powder to the solution. At lower hematocrit (<2%), carbon particles were added (Indian ink) to attenuate signal amplitude further. The solution homogeneity was maintained with mild agitation using a magnetic stirrer. The probe from the device was attached to the vessel surface as shown. Distance between photon source and detector was 40 mm.

Results and Discussion

FIG. 2B shows a spectrum with three traces, for a solution of 5% Hct. The lower trace is for the calculated value of 810 nm-750 nm, derived from the top two traces (750 nm and 810 nm signals). A changing voltage level in the 750 nm and the 810 nm-750 nm traces accompanied oxygen supply withdrawal as the hemoglobin gave up the oxygen to the yeast at a constant rate. A linear change in the signal over the full blood-oxygen saturation range is evident, see linear dotted line.

In contrast, the 810 nm signal (top trace) remained insensitive to the changing blood-oxygen level, consistent with it being the isosbestic wavelength.

Hence the 850 nm-750 nm signal represents the blood-oxygen index while the 810 nm signal represents blood volume index. In subsequent blood-oxygen calculations in sleep studies 750 nm -810 mm was found to be particularly suitable, as use of a calibration factor in further Examples allowed the voltage signal of the 750 nm value to remain positive.

As almost all deoxyhemoglobin is in the venous compartment of the vasculature (with normal pulmonary and cardiac function), the signal, 750 nm-810 nm, provides an index of venous blood-oxygen (SvO2) proportion. This assumes an arterial oxyhemoglobin value greater than 95%. This is not the case during respiratory insufficiency, in which case the blood-oxygen index is proportional to the global blood-oxygen saturation in the measured light path.

EXAMPLE 3

Interpretation of Spectra Acquired by the Monitoring Apparatus: Analysis of Apnea Events The apparatus schematically depicted in FIG. 3C was used for detecting respiratory parameters in a patient. FIG. 6 shows multiple peaks in both blood volume and blood oxygen while the subject is on their back. These are multiple mild apnea events, not present when the patient is lying on their side. Over the approximately 24 minutes of repeated apnea events there were no cumulative changes in blood volume or blood oxygen levels (average voltage maintained).

This suggests each brief recovery period was sufficient to return both oxygen saturation and blood volume to quiescent conditions, resulting in little oxygen stress. Examining the trace at briefer time intervals, enables the counting the number of these apnea events over time and thus a score of apnea or hypopnea events per hour can be obtained, as required for standard diagnostic criteria of sleep-disordered breathing.

Figure 7:
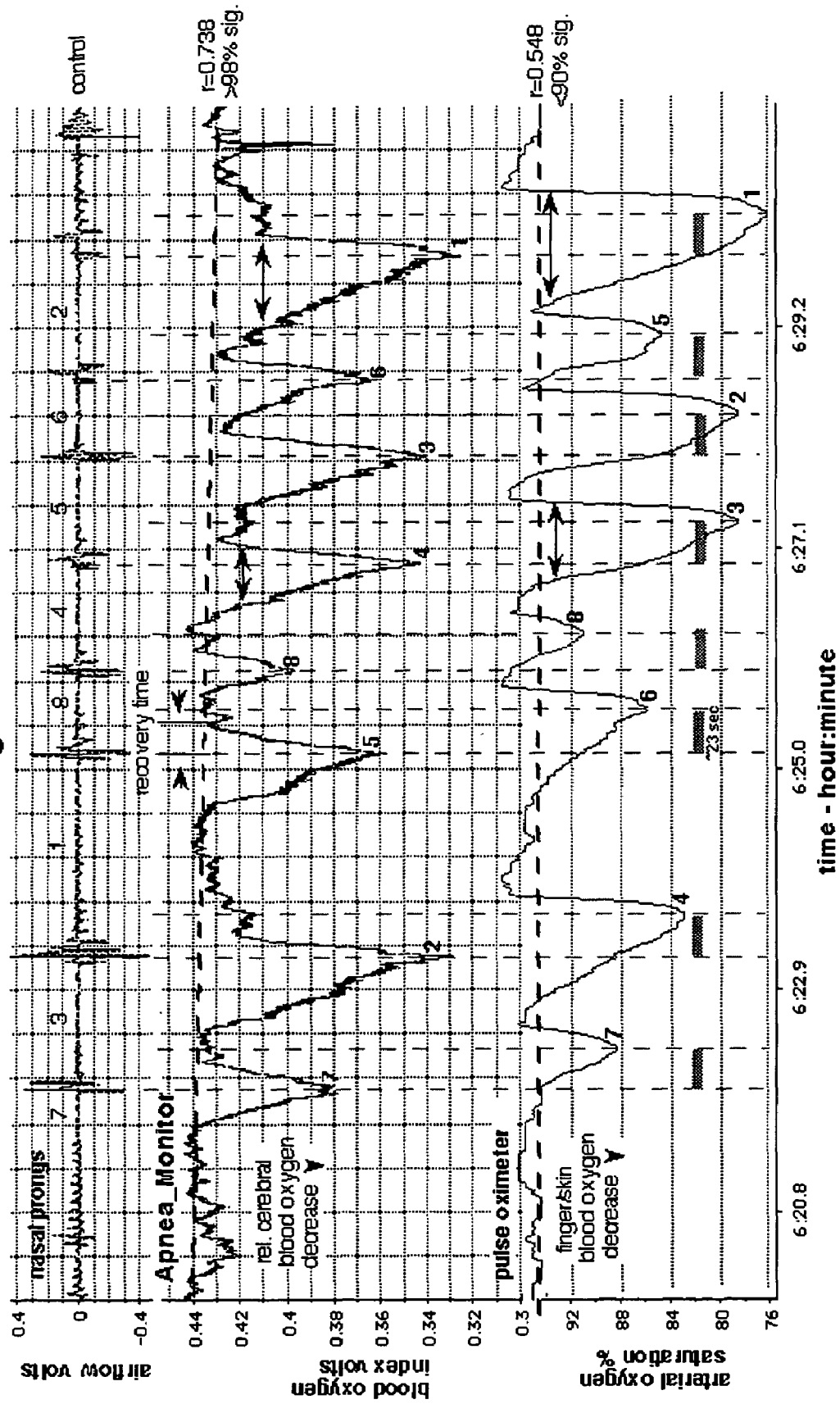
FIG. 7 is a graphical representation showing sample comparative respiratory data.

Three traces recording a series of deep apnea events in a patient, recorded over an approximate time period of ten minutes, are shown in FIG. 7. The top trace is the respiratory airflow (pressure signal) from nasal prongs, the second and third traces are from the blood-oxygen index acquired by the apparatus depicted schematically by FIG. 3C, and the arterial blood oxygen saturation (pulse oximeter) respectively. The pulse oximeter was affixed to the subject to measure finger, arterial-blood oxygen saturation.

Using the nasal prong signal as the standard, each apnea event is ranked according to the period for no nasal airflow (absence of signal cycling). Given constant body metabolism, the level of blood-oxygen desaturation should be proportional to the time of no respiration shown by the airflow transducer. The 'depth' of each apnea event should correlate with the time for which no air is exchanged in the lung.

The signals from both the apparatus according to FIG. 3C and the pulse oximeter are ranked according to the depth of desaturation. Using a Spearsman's ranking correlation test, the desaturation levels were each compared to the ranking shown in the nasal prong's trace.

There was a significant correlation between the response of the airflow transducer as a measure of apnea severity to that of the desaturation signal measure using the apparatus shown in FIG. 3C (>98% CI), whereas the correlation between the nasal prong's rank and the pulse oximeter's desaturation rank is not significant (<90%). This is consistent with the claims of poor linearity for pulse oximetry with deep hypoxia, or a consequence of measuring peripheral low metabolizing tissue. As the oximeter's measurement was from the finger, there was a 23-second phase shift (lag) compared to the desaturations observed with the study apparatus.

The slope of the dotted line through the trace in FIG. 7 demonstrates a reducing base line consistent with a reduction in global saturation, not compensated for during each apnea's brief recovery phase. This is consistent with incurring an oxygen debt over the 10 minute period of multiple apneas. This contrasts to the much longer apnea cycle presented in FIG. 6, where there was no long term build up in oxygen debt.

Using the conventional scoring technique, the series of apnea events for the results in FIG. 6 were found to score more highly than for the apnea series illustrated in FIG. 7. Oxygen tissue stress is far more likely, along with potential adverse neurological consequences for the subject in FIG. 7, despite a lower score.

An oxygen debt index can be calculated based on the slope of the decrease in blood oxygen (dotted line) multiplied by the time period for which blood-oxygen remained below the quiescent value. This would draw a sharper distinction between adverse effects resulting from repeat arousals and effects due to periods of hypoxia.

The thin vertical dotted lines in FIG. 7 show alignment of respiration restart with recovery from hypoxia at each apnea event, 7±2 seconds. It is likely that the rate of response to resaturation correlates with pulmonary efficiency. A possible outcome would be to see a longer recovery time in patients with compromised pulmonary efficiency/function, such as a heavy smoker. This response time would also have diagnostic value.

Oxygen debt was not apparent in the arterial oxygen saturation trace recorded by the pulse oximeter.

EXAMPLE 4

Blood Volume Cycling Due to Respiratory Insufficiency

Figure 8:
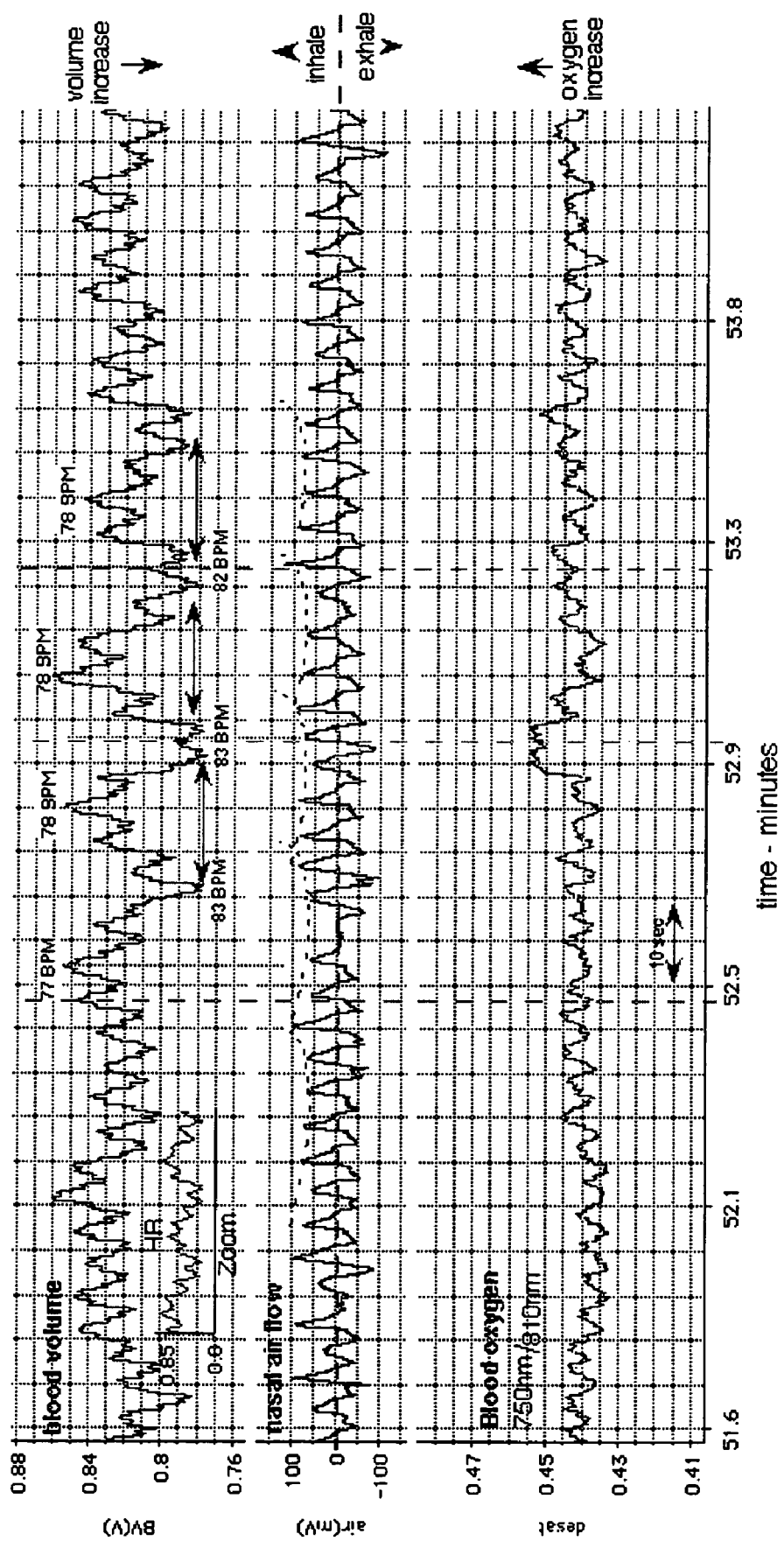
FIG. 8 is a graphical representation of respiratory data showing blood volume cycling in response to a hypopnea event.

FIG. 8 shows a three minute segment of signals from the apparatus schematically depicted in FIG. 3C, and the nasal airflow transducer monitoring, during a sleep study.

The top trace is of blood volume index in which approximately 15 second cycling was occurring. An expanded segment of the trace resolves systole pulsatile flow (top right in blood volume trace) from which the heart rate was calculated. Beats per minute (BPM) for peaks and troughs were calculated in the cycling blood volume. The cycles evident in the blood volume can just be distinguished within the airflow trace, shown by dotted lines.

There was little evidence in the blood-oxygen signal (bottom trace) of oxygen deficiency. In part this could be attributed to the cyclic increases in blood volume compensating respiratory decreases. By examining heart rates in the blood volume trace, it was evident that the blood volume cycling was a response (at least in part) to a varying heart rate of 5%. It also seems probable that the heart response was not triggered by blood oxygen insufficiency in cerebral tissue. So the cycling flow could be attributed to increased/decreased cardiac output rather than a local vascular dilation/contraction response, the cyclic variation in the airflow signal provides supportive evidence that this blood cycling was not artefact.

It is difficult to know how to classify these events as most likely they go undetected so unreported in sleep studies. The cycling is likely to have been induced by respiratory resistance such as pre- or mild hypopnea.

EXAMPLE 5

(i) Acquiring Hypopnea Events in Sleep Studies

Generally, attempts are made to score hypopnea events as part of the overall diagnosis of sleep apnea. It is difficult to estimate pathologies that may result from repeated nightly hypopnea events. Although inducing repeated arousals is an obvious detrimental effect which often accompanies hypopnea.

Figure 9:
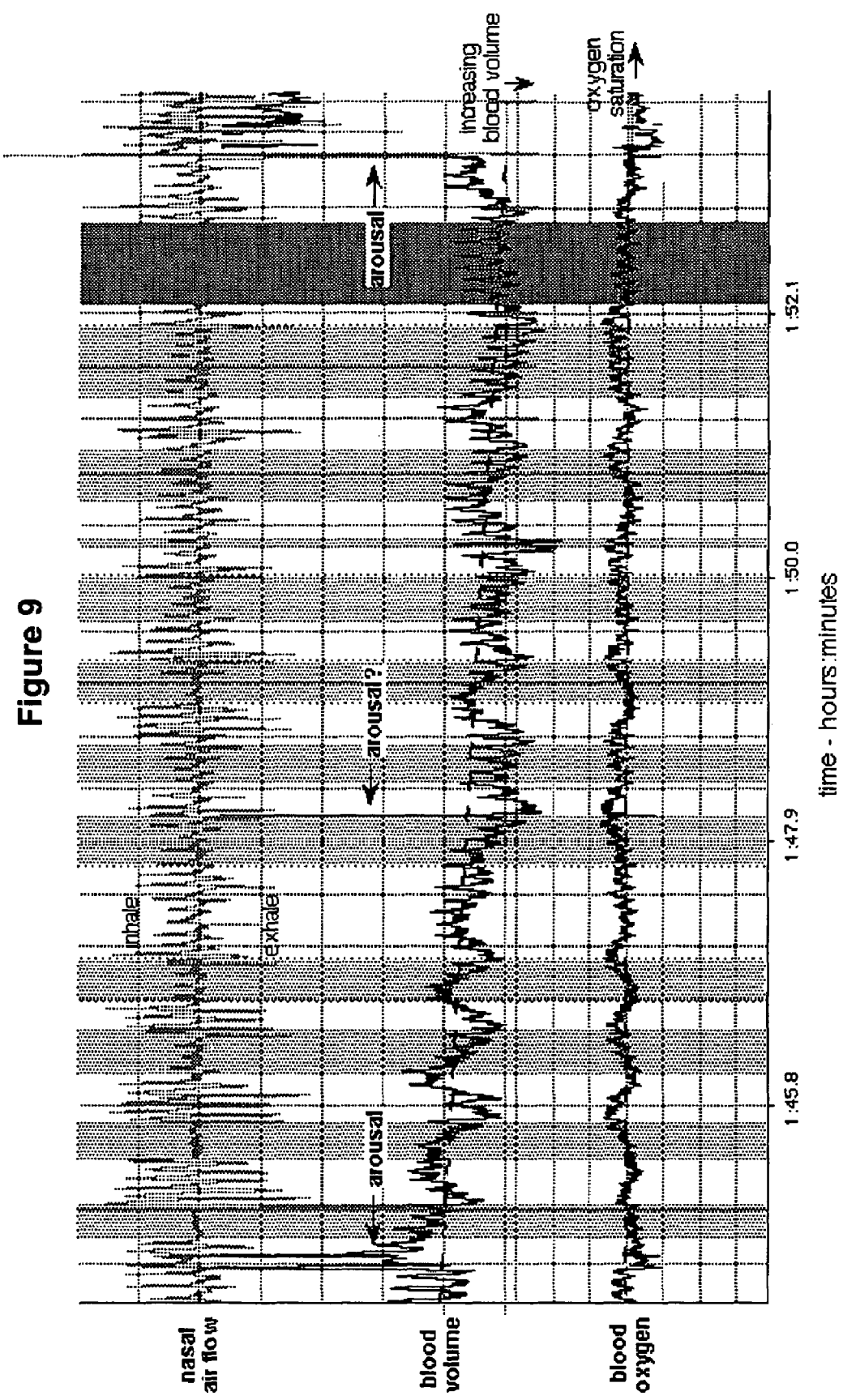
FIG. 9 is a graphical representation of respiratory data during hypopnea.

FIG. 9 shows a 10 minute segment from a sleep study in which nasal airflow and the signals from the device in FIG. 3A are shown. There is evident respiratory cycling. The hatched vertical regions show alignment for all three signals. It is evident that cycling in the blood volume index was responding to the respiration insufficiency. The dotted line through the blood volume indicates an increase in blood volume, especially in the first five minutes. There is no evidence of a drop in cerebral blood oxygen, suggesting that increased flow adequately compensates reduced respiratory efficiency. The minor cycling within the bottom trace is consistent with blood-oxygen changes with the cycling blood flow. Rapid vertical movements in the blood volume trace near the start and end of the sequence were consistent with arousal's. These hydrostatic shifts to head movement were effectively suppressed in the blood oxygen trace by the algorithm used (750 nm×k-810 nm). The arousals would appear not to be in response to cerebral blood oxygen falls.

(ii) Measuring Arousals in Response to Apnea Events

One of the characteristics of sleep apnea is the repeated arousals in response to respiratory blockage or insufficiency.

Figure 10:
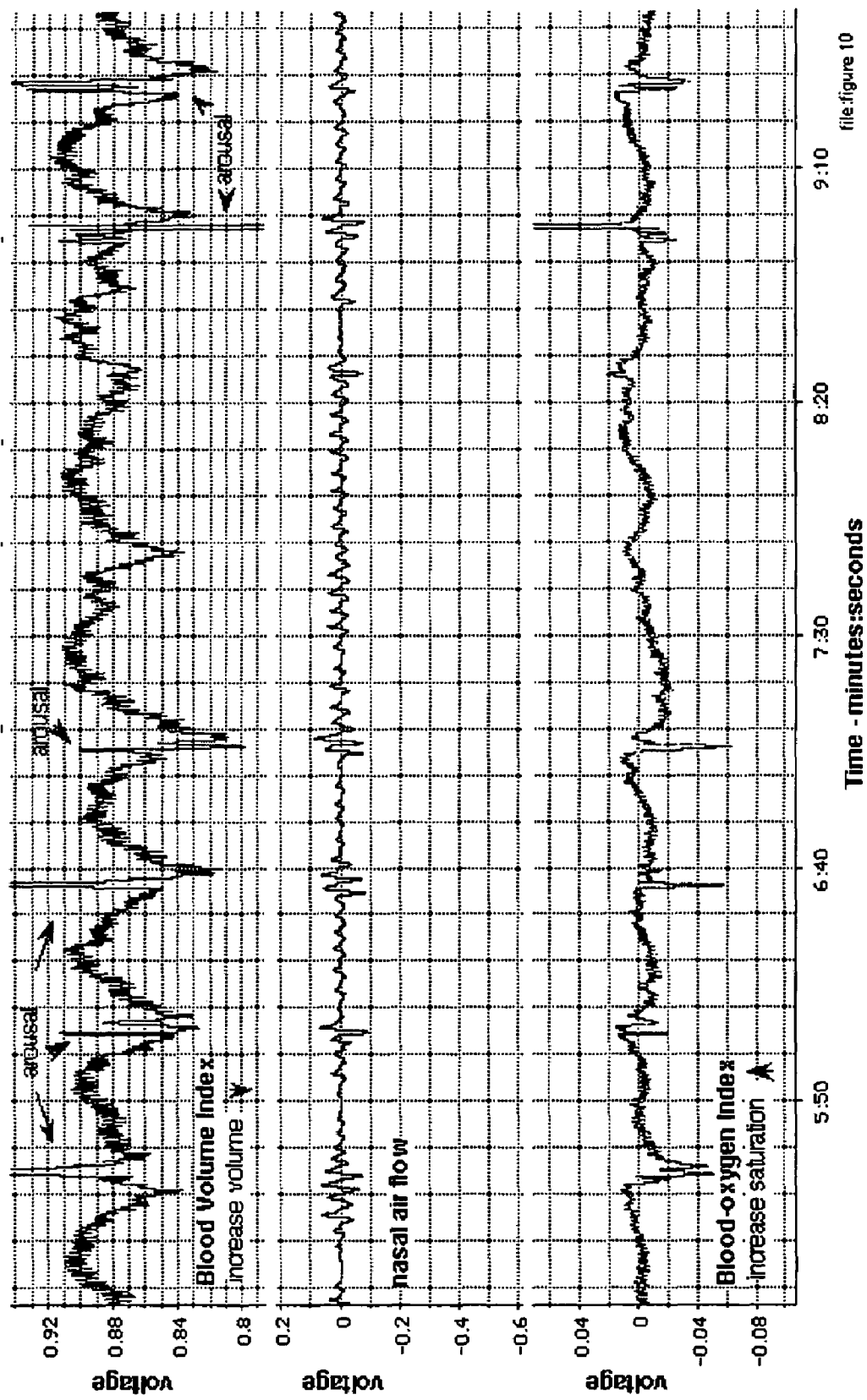
FIG. 10 is a graphical representation of respiratory data during hypopnea.

FIG. 10 is a five minute segment of hypopnea from a sleep study whose characteristic is similar to that in FIG. 9, although the patient data in FIG. 10 indicates a number of arousals which are evident on the blood oxygen trace. These transitions are large enough to have an effect on the calculated blood-oxygen signal, although this may in part be vascular adjustment.

These arousals are not evident in the airflow trace and not all were picked up by a leg-mounted accelerometer transducer. This is likely to occur because arousals may arise as head movement only, so a body or leg movement transducer may not provide an accurate score of arousals', compared to the apparatus and methods of the present study.

Figure 11:
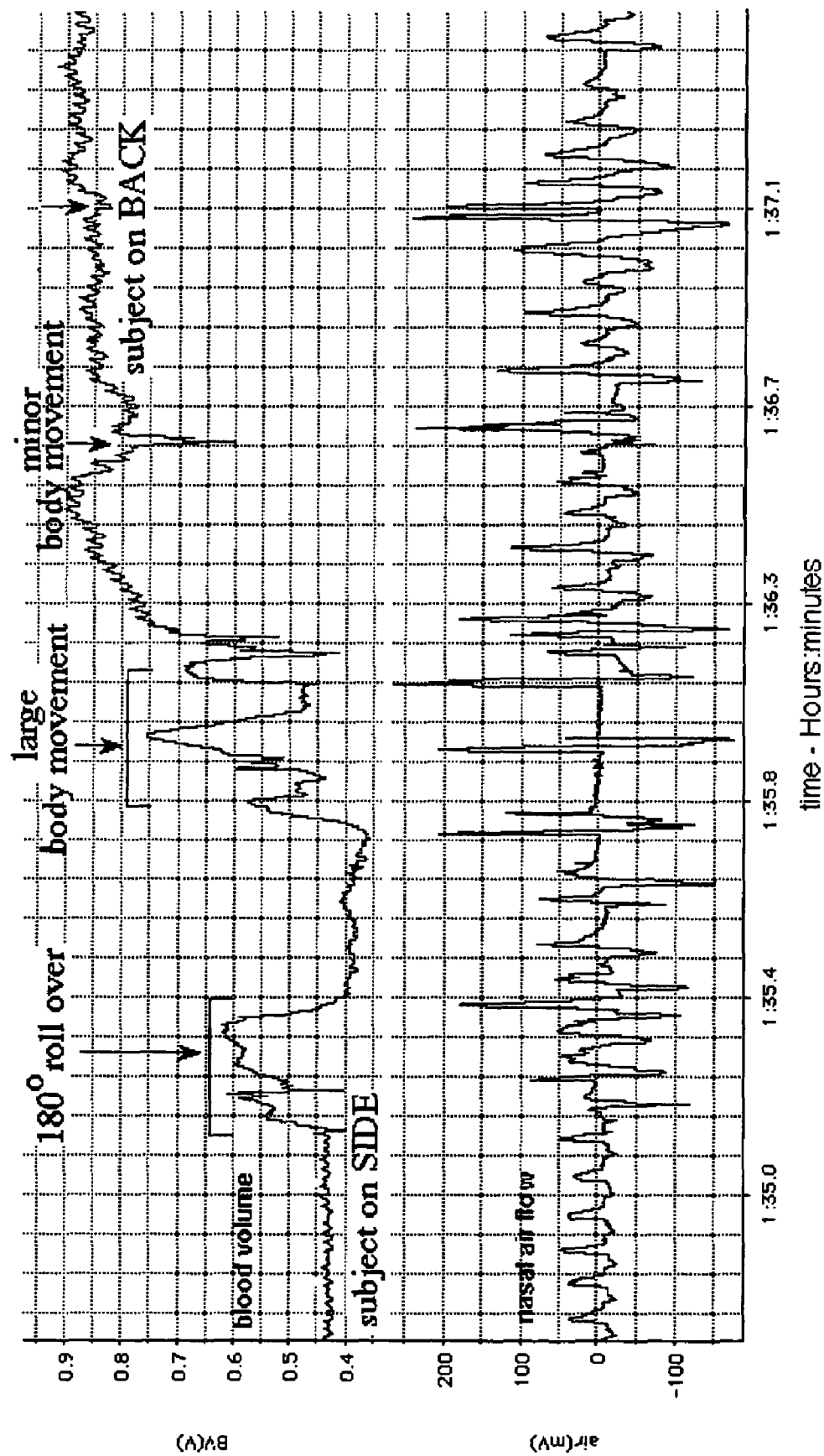
FIG. 11 is a graphical representation of interference in a nasal air flow reading caused by patient arousal during sleep but accurately interpreted as postural movements in the blood volume trace.

FIG. 11 suggests that some arousals involving large body movement interfere with the airflow transducer signal. Signals on the airflow trace may well be interpreted as deep inhalation/exhalations or apnea events. While nuances within the blood volume signal are lost during large body movements, they are not likely to be misinterpreted as apnea events.

EXAMPLE 6

Scoring Respiratory Events

It is evident in FIG. 8 that the correlation of blood volume peaks are synchronous with respiration. In general, the peak amplitude in the blood volume signal correlates to that of the nasal prong's, which fluctuate with the depth of respiration, when movement artifact is absent.

Figure 12B:
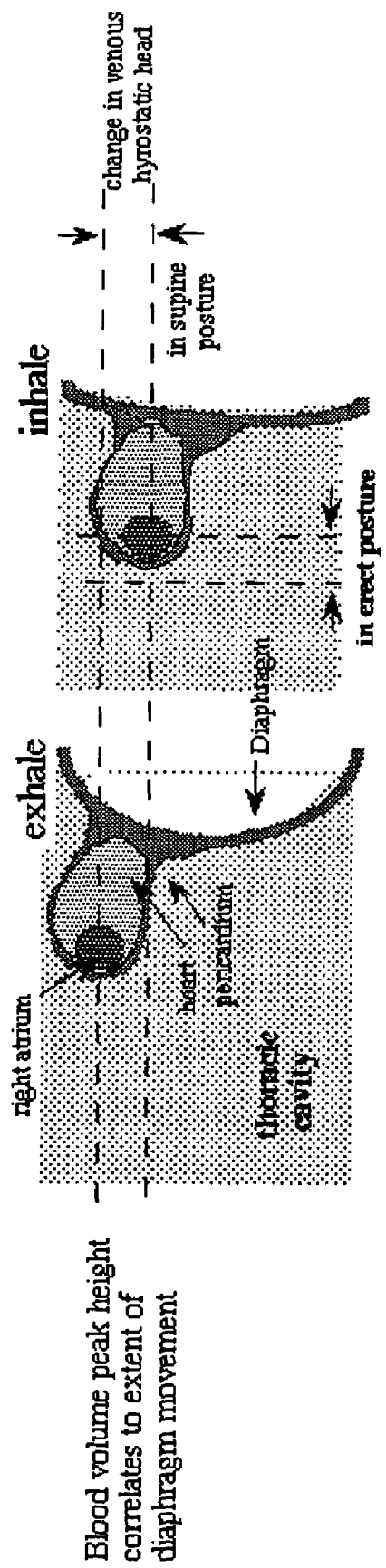
FIG. 12B is a schematic representation of blood volume and venous hydrostatic head changes in a patient.

A probable source of blood volume changes, in synchrony with respiration, in the signals detected according to the present invention is with heart movements. FIG. 12 shows the phase relationship between respiratory airflow and the tracking by the blood volume signal. As with the respiratory signal, the rise times are faster than fall rates in the peaks. For the most part, amplitudes of the blood volume peaks correlate with that in the respiratory peaks. These peaks have lower amplitude in a subject who is standing and are absent from signals acquired from limb muscle.

Based on the much lower amplitude recorded in blood-oxygen trace, their likely source is blood hydrostatic head changes. Heart displacement is induced by its being coupled to the diaphragm muscle via the pericardium so moving in sympathy with respiration. The changes in hydrostatic head are illustrated in the diagram in FIG. 12. Hence, respiratory events involving diaphragm contraction and relaxation can be monitored by the methods and apparatus of the present invention.

Figure 13:
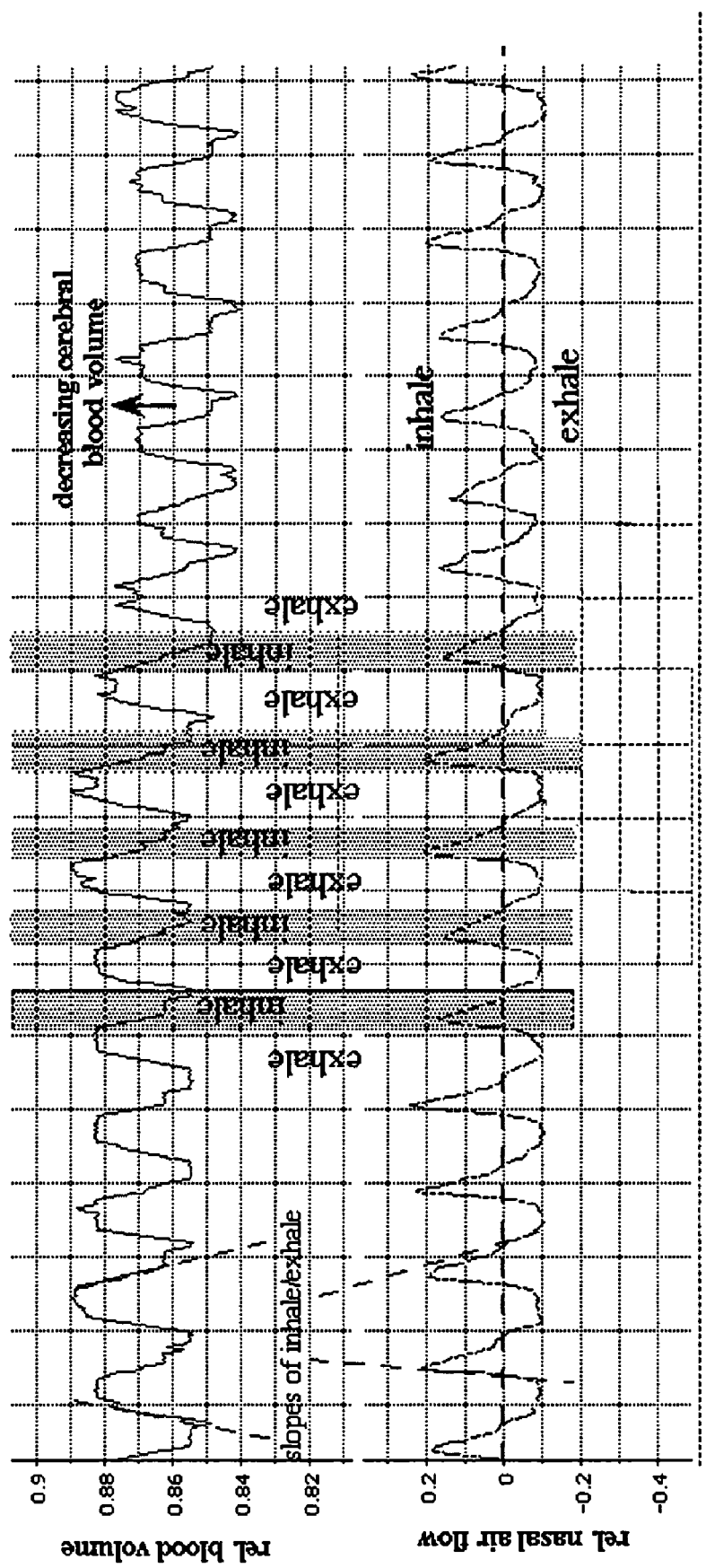
FIG. 13 is a graphical representation of blood volume and nasal air flow during apnea.
Figure 14:
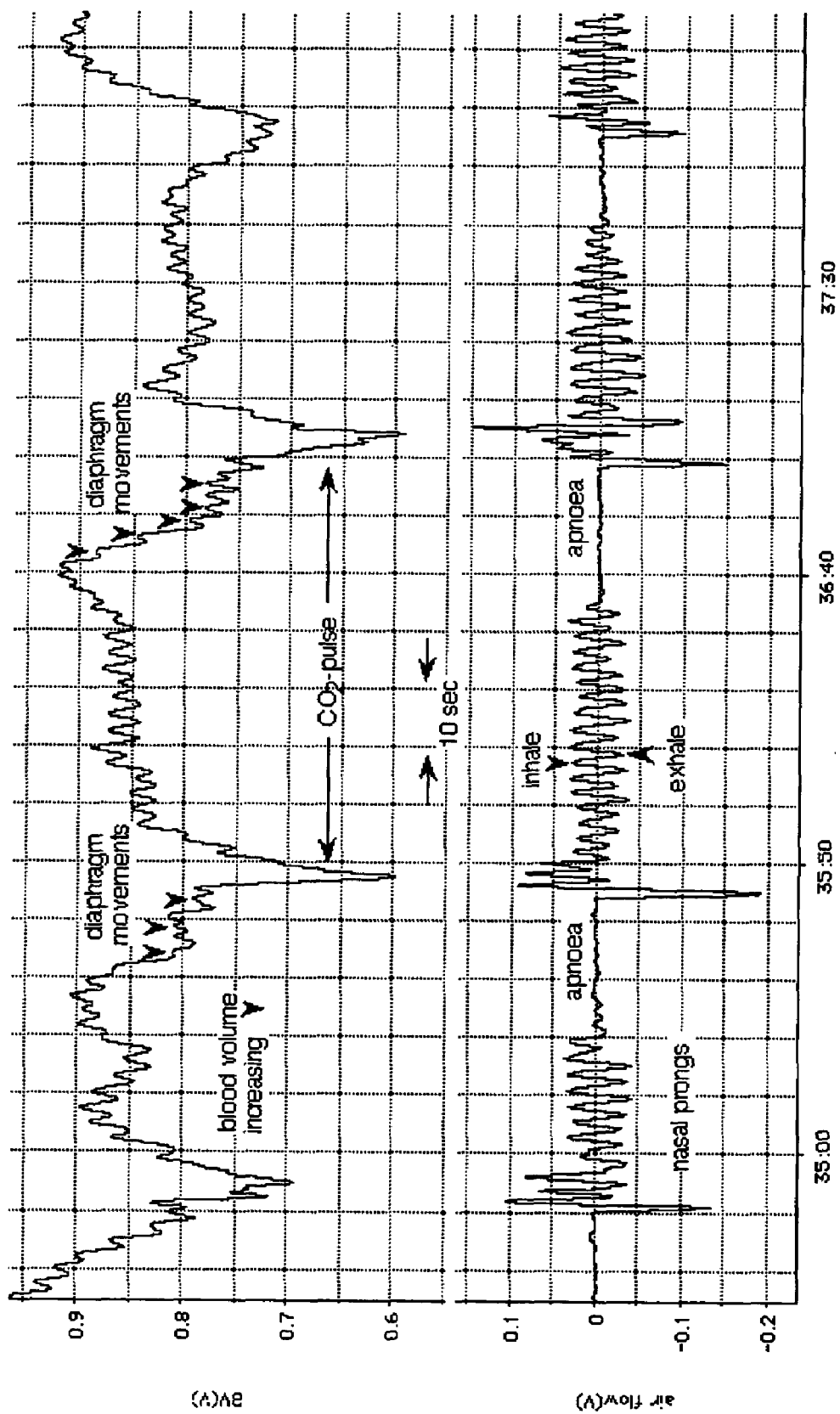
FIG. 14 is a graphical representation of blood volume and nasal air flow during obstructive sleep apnea.

The difference between obstructive sleep apnea and central sleep apnea is the lack of movement of respiratory muscle with the latter. This can be observed in FIG. 13 where a two-minute sequence of a blood volume trace and nasal prong trace are compared during apnea events. Based on the blood volume trace it is observed that the respiratory cycling is absent during the apnea periods (based on the nasal prongs). The vertical dotted lines shows alignment between the respiratory activity for both transducers. In contrast, FIG. 14 characterises obstructive sleep apnea, where respiratory effort persists during apnea events.

What is claimed is:

1. A method of detecting disordered respiration in a patient, the method comprising:

(a) exposing the patient's cerebral tissue to radiation, the radiation having at least first and second predetermined wavelengths, the first and second predetermined wavelengths being between about 730 nm to 770 nm, and 790 nm to 830 nm, respectively;
(b) sensing the levels of radiation reflected by the cerebral tissue at the first and second predetermined wavelengths;
(c) in a calibration step:
(i) determining reflection levels for first and second patient orientations; and,
(ii) using the determined reflection levels to determine a calibration factor; and
(d) in a monitoring step:
(i) calculating a blood oxygen index in accordance with the sensed reflected radiation and the calibration factor; and,
(ii) detecting a presence or absence of disordered respiration in the patient based at least in part on changes in the blood oxygen index determined in accordance with the calibration factor.

2. The method according to claim 1, wherein the disordered respiration is a sleep-related respiratory deregulation.

3. The method according to claim 2, wherein the sleep-related respiratory deregulation is obstructive sleep apnea, central sleep apnea or both.

4. The method according to claim 1, wherein the first and second patient orientations include:
(e) the patient lying on their back; and,
(f) the patient lying on their side.

5. The method according to claim 1, wherein the blood oxygen index is determined in accordance with the equation:

$$|B-A|$$

wherein:
A is the reflected level at the first predetermined frequency; and,
B is the reflected level at the second predetermined frequency.

6. The method according to claim 1, wherein the blood oxygen index is determined in accordance with one of the following equations:

$$|B-kA| \text{ or } [Ak-B]$$

wherein:
k is the calibration factor.

7. The method according to claim 6, wherein the calibration factor is determined empirically so as to reduce effects of a hydrostatic head change effect on the blood oxygen index.

8. The method according to claim 1, wherein first and second light-emitting diodes (LEDs) are used to generate the first and second wavelengths respectively.

9. The method according to claim 8, wherein the method further includes a photodiode to sense absorbed radiation.

10. The method according to claim 1, said method further including:
a) selectively exposing the patient's cerebral tissue to radiation;
b) sensing reflected radiation when the patient's cerebral tissue is exposed, to determine an exposed level;
c) sensing radiation when the patient's cerebral tissue is not exposed to determine an ambient radiation level; and,
d) determining a reflected level by subtracting the ambient radiation level from the exposed level.

11. The method according to claim 1, wherein the reflected values for the first and second wavelengths and ambient light are consecutively sampled at least 30 times per second.

12. The method according to claim 1, wherein the method includes using algorithms to calculate parameters selected from the group consisting of oxygen debt accumulation value during insufficient respiration, hypoxic value of apnea events, pulsatile flow, blood volume cycling, diaphragm movements during respiration patient wherein a movement is indicative of obstructive, central or mixed type sleep apnea, arousals during an unconscious state and recovery time to quiescent saturation.

13. The method according to claim 1, wherein the monitoring step is performed for a predetermined time period.

14. A method of monitoring flow response times to hydrostatic pressure adjustments in a patient, the method comprising:
(a) exposing the patient's cerebral tissue to radiation, the radiation having at least first and second predetermined wavelengths, the first and second predetermined wavelengths being between about 730 nm to 770 nm, and 790 nm to 830 nm respectively;
(b) sensing the levels of radiation absorbed by the cerebral tissue at the first and second predetermined wavelengths;
(c) in a calibration step:
(i) determining absorption levels for first and second patient orientations; and,
(ii) using the determined absorption levels to determine a calibration factor; and
(d) in a monitoring step:
(i) calculating a blood oxygen index in accordance with the sensed absorbed radiation and the calibration factor; and,
detecting a flow response time to a hydrostatic pressure adjustment in the patient based at least in part on changes in the blood oxygen index determined in accordance with the calibration factor.

15. An apparatus for detecting disordered respiration or a flow response time to a hydrostatic pressure adjustment in a patient, the apparatus comprising:
(a) a radiation source for exposing the patient's cerebral tissue to radiation, the radiation having at least first and second predetermined wavelengths, the first and second predetermined wavelengths being between about 730 nm to 770 nm, and 790 nm to 830 nm respectively;
(b) a sensor for sensing the level of radiation reflected by the cerebral tissue at the first and second predetermined wavelengths; and,
(c) a processor for:
(i) in a calibration step:
(a) determining reflected radiation levels for first and second patient orientations; and,
(b) using the determined absorption levels to determine a calibration factor; and
(ii) in a monitoring step:
(a) calculating a blood oxygen index in accordance with the sensed absorbed radiation and the calibration factor; and,
(b) detecting a presence or absence of disordered respiration in the patient based at least in part on changes in the blood oxygen index determined in accordance with the calibration factor.

16. The apparatus according to claim 15, wherein the radiation source includes first and second LEDs for generating the first and second predetermined wavelengths, respectively.

17. The apparatus according to claim 16, wherein the sensor includes a photodiode for sensing the reflected radiation.

18. The apparatus according to claim 15, further including a controller for controlling the operation of the radiation source and the sensor.

19. The apparatus according to claim 18, wherein the controller is adapted to:
  (a) selectively activate the radiation source to thereby expose the patient's cerebral tissue to radiation;
  (b) selectively sample signals from the sensor to thereby sense radiation when:
    (i) the patient's cerebral tissue is exposed to determine an exposed radiation level;
    (ii) the patient's cerebral tissue is not exposed to determine an ambient radiation level; and,
  (c) determine a reflected level by subtracting the ambient level from the exposed level.

20. The apparatus according to claim 19, wherein the controller is adapted to cause reflected values for the first and second wavelengths and ambient light to be consecutively sampled at least 30 times per second.

21. The apparatus according to claim 20, wherein the controller includes:
  (a) a processor for controlling the radiation source and a sampling time interval of the sensor; and,
  (b) a memory for storing reflected level signal values.

22. The apparatus according to claim 21, wherein the processor is adapted to control a pulsed radiation source.

23. The apparatus according to claim 21, wherein the processor is adapted to perform at least some processing of the reflected level signal values.

24. The apparatus according to claim 21, wherein the controller includes a communication means for transferring data to a remote processing system, the remote processing system being adapted to perform at least some processing of the reflected level signal values.

25. The apparatus according to claim 24, wherein the remote processing system is adapted to display a reflected level.

26. The apparatus according to claim 18, wherein the apparatus includes a user input for controlling the controller.

27. The apparatus according to claim 26, wherein the user input is used for selectively activating at least one of the calibration step and the monitoring step.

28. The apparatus according to claim 27, wherein the controller is provided in a housing.

29. The apparatus according to claim 28, wherein the housing is suitable for home use by a patient.

30. The apparatus according to claim 28, wherein the radiation source and the sensor are provided in a probe coupled to the housing, the probe being adapted for attachment to the patient in use.

31. The apparatus according to claim 30, wherein the probe is formed from silicon rubber.

* * * * *